(12) United States Patent
Williamson et al.

(10) Patent No.: US 8,703,952 B2
(45) Date of Patent: Apr. 22, 2014

(54) SYNTHESIS OF 9-(ARYLALKYL)-1,2,3,4-TETRAHYDRO-γ-CARBOLINE AND ANALOGUES AND INTERMEDIATES

(75) Inventors: Craig Williamson, Old Aberdeen (GB); John Mervyn David Storey, Old Aberdeen (GB)

(73) Assignee: WisTa Laboratories Ltd., Singapore (SG)

(*) Notice: Subject to any disclaimer, the term of this patent is extended or adjusted under 35 U.S.C. 154(b) by 243 days.

(21) Appl. No.: 13/133,900

(22) PCT Filed: Dec. 11, 2009

(86) PCT No.: PCT/GB2009/002873
§ 371 (c)(1),
(2), (4) Date: Jun. 9, 2011

(87) PCT Pub. No.: WO2010/067085
PCT Pub. Date: Jun. 17, 2010

(65) Prior Publication Data
US 2011/0245504 A1    Oct. 6, 2011

Related U.S. Application Data

(60) Provisional application No. 61/122,105, filed on Dec. 12, 2008.

(51) Int. Cl.
*C07D 491/00* (2006.01)
*A61K 31/44* (2006.01)

(52) U.S. Cl.
USPC ............................................. 546/87; 514/292

(58) Field of Classification Search
None
See application file for complete search history.

(56) References Cited

U.S. PATENT DOCUMENTS 3,409,628 A   11/1968   Berger et al.
5,411,977 A   5/1995    Petraitis et al.

FOREIGN PATENT DOCUMENTS

EP    0 409 163 A2    1/1991

OTHER PUBLICATIONS

International Search Report and Written Opinion received in the corresponding International Patent Application No. PCT/GB2009/00873, dated Jun. 25, 2010.

*Primary Examiner* — Heidi Reese
(74) *Attorney, Agent, or Firm* — Foley & Lardner LLP

(57) ABSTRACT

The present invention pertains generally to methods of preparing certain 9-(arylalkyl)-1,2,3,4-tetrahydro-γ-carboline compounds and their analogues, and especially to methods of preparing dimebon. The present invention also pertains to methods of preparing certain intermediate compounds which find use in the synthesis of the 9-(arylalkyl)-1,2,3,4-tetrahydro-γ-carboline compounds.

27 Claims, No Drawings

SYNTHESIS OF 9-(ARYLALKYL)-1,2,3,4-TETRAHYDRO-γ-CARBOLINE AND ANALOGUES AND INTERMEDIATES

CROSS-REFERENCE TO RELATED PATENT APPLICATIONS

This application is the U.S. National Phase of PCT/GB2009/002873, filed Dec. 11, 2009, which was published in English on Jun. 17, 2010, as WO 2010/067085 A2, and which claims priority from U.S. Provisional Application No. 61/122,105, filed Dec. 12, 2008, all of which are incorporated herein by reference in entirety.

TECHNICAL FIELD

This invention pertains generally to processes, methods and materials for the preparation of particular pyridoindole compounds, such as dimebon. These compounds are useful as drugs, for example, in the treatment of tauopathies, such as Alzheimer's disease.

BACKGROUND

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Dimebon, also referred to as dimebolin, and its structurally related analogues have been shown to inhibit the death of brain cells in preclinical models of Alzheimer's disease (AD) (see, for example, Medivation Form 10KSB filed 19 Feb. 2008). Treatment of patients having mild-to-moderate AD in a randomised, double-blind, placebo-controlled study with dimebon is reported as resulting in significant benefits in assessed cognition, as measured in the cognitive subscale of the Alzheimer's disease assessment scale (ADAS-cog) (see Doody et al.). It is suggested that dimebon is safe, well tolerated, and is capable of improving the clinical course of subjects having AD at a mild to moderate level. Further clinical trials are underway for the use of Dimebon against Alzheimer's disease and for Huntington's disease (see Medivation press release 4 Nov. 2009).

Dimebon has also been reported to be an inhibitor of TDP-43 proteinopathy in cellular models of amyotrophic lateral sclerosis (ALS) and frontotemporal lobar degeneration with ubiquitinated inclusions (FLTD-U) (see Yamashita et al.).

Dimebon has the structure shown below, where the atoms in the pyridoindole group are labelled for reference:

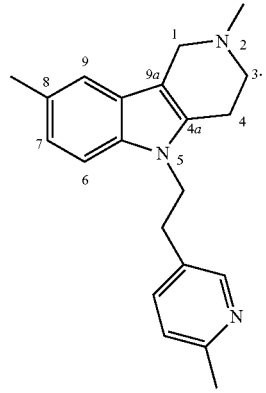 [SMILES: Cc1ccc2c(c1)c1c(n2CCc2ccc(C)nc2)CCN(C)C1]

A key intermediate in the synthesis of Dimebon and its analogues is [2-(6-methyl-pyridin-3-yl)-ethyl]-p-tolyl-amine (compound (1)). This compound may be prepared from 2-methyl-5-vinylpyridine (2) and p-toluidine (3), as described, for example, in U.S. Pat. No. 3,409,628 (see Example 14):

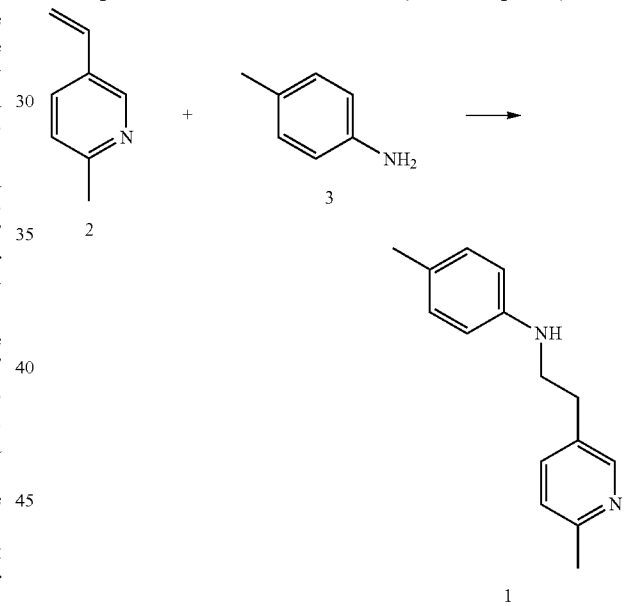

Compound 1 may be converted to the dimebon analogue 6 having a benzyl substituent at the pyridoindole 2-position:

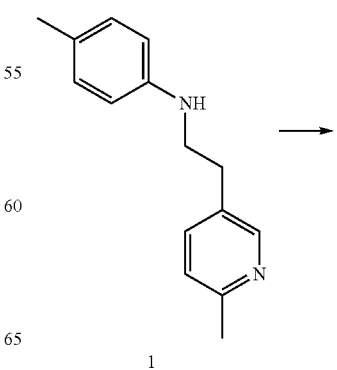

-continued

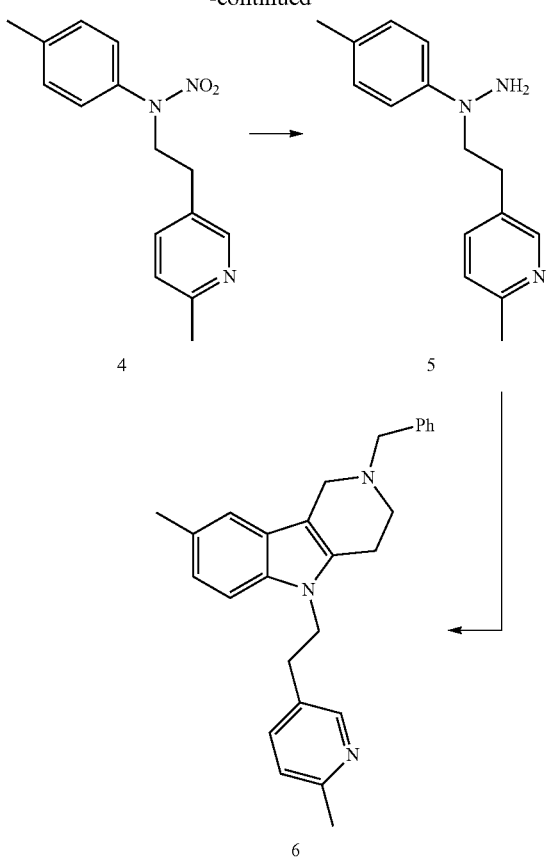

4

5

6

Similarly, Kost et al. (*J. Gen. Chem. USSR* 1960, 30, 2538) describe the use of 2-methyl-5-vinylpyridine for the preparation of related tetrahydrocarbazole structures, such as compound 7:

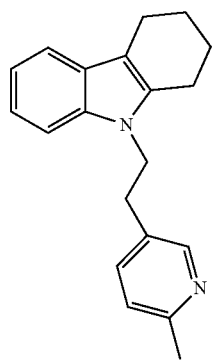

7

The synthesis proceeds via 2-methyl-5-(2-phenylaminoethyl)pyridine, an analogue of compound 1.

The synthesis of dimebon is described by Kost et al. (*Chemistry of Heterocyclic Compounds*, 1973, 9, 191). Dimebon, referred to as 9-[2-(2'-methyl-5'-pyridyl)ethyl]-3,6-dimethyl-1,2,3,4-tetrahydro-γ-carboline, is prepared by the direct reaction of 2-methyl-5-vinylpyridine with the carboline (i.e. 3,6-dimethyl-1,2,3,4-tetrahydro-γ-carboline) in the presence of a very strong base, for example sodium ethoxide.

More recently, Ivachtencko et al. (*Bioorg. Med. Chem. Lett.*, 2009, 19, 3183-3187) have synthesised Dimebon and analogues by a similar method, in which the tricyclic ring system (carboline) is formed and reductively aminated with 2-methyl-5-vinylpyridine, in the presence of base and a phase transfer catalyst.

However, 2-methyl-5-vinylpyridine is not available commercially, and must be prepared as required. 2-Methyl-5-vinylpyridine may be obtained from 5-ethyl-2-methylpyridine by oxidation over a heterogeneous catalyst, typically at elevated temperature. However, the use of sustained high temperatures means that this method is not suitable for the large scale production of 2-methyl-5-vinylpyridine.

For example, U.S. Pat. No. 2,611,769 describes the preparation of 2-methyl-5-vinylpyridine from 5-ethyl-2-methylpyridine at temperatures of 600° C. and above. The amount of product obtained is low, around 16%, and requires separation from unreacted starting material.

U.S. Pat. No. 2,716,119 also describes the preparation of 2-methyl-5-vinylpyridine from 5-ethyl-2-methylpyridine. The reaction step is performed at a temperature of around 700° C. and provides around 25 to 40% yield of material depending on the heterogeneous catalyst chosen.

Furthermore, the preparation of compound 1 from 2-methyl-5-ethylpyridine is reported as requiring the use of sodium metal (see, for example, U.S. Pat. No. 3,409,628). The use of this flammable/pyrophoric metal makes this method undesirable for a large scale synthesis.

Given the recently reported benefits of dimebon, there is a need for alternative methods of synthesis that can be reproduced on a large scale and/or provide increased yields of product. In addition, the methods of the invention avoid the need for complex gas phase reactions and pyrophoric reagents. Specialist equipment and procedures are therefore not needed in the present invention, and the overall cost of the synthesis may thereby be reduced.

The present inventors have established an alternative route to the key intermediate that avoids the use of high temperature oxidation and avoids the use of sodium metal.

SUMMARY OF THE INVENTION

The present inventors have now identified certain methods and compounds for use in the synthesis of dimebon and its analogues. These methods and compounds may also find use in the synthesis of intermediates that are themselves suitable for use in the synthesis of dimebon and its analogues.

The methods have certain other properties, for example by comparison with the methods of the prior art discussed above.

In other aspects of the invention there are provided compounds of formula (II), (III), (IV), (V), and (VI), and particularly their use in the synthesis of dimebon or its analogues.

In other aspects there are provided compounds of formula (I), (II), (III), (IV), (V), and (VI) obtained or obtainable by the methods described herein. In other aspects, the invention pertains to compounds obtained or obtainable by the methods described herein for use in therapy.

Methods of Synthesis

In a general aspect the present invention provides methods for the synthesis of a compound of formula (I):

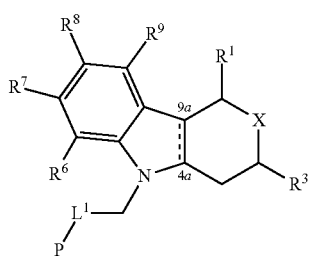
(I)

wherein
—$R^1$ and —$R^3$ are each independently —H or —$R^A$;
X is independently selected from $CH_2$, $CHR^A$, $CR^A_2$, NH, $NR^A$, O, S, S(O) and $S(O)_2$;
—$R^6$, —$R^7$, —$R^8$, and —$R^9$ are each independently —H or —$P^A$;
-$L^1$- is independently linear saturated $C_{1-6}$alkylene;
—P is independently pyridine or phenyl, optionally substituted with one or more groups —$P^A$;
each —$R^A$ is independently:
  —$R^{A1}$, —$R^{A2}$, —$R^{A3}$, —$R^{A4}$, —$R^{A5}$,
  -$L^A$-$R^{A2}$, -$L^A$-$R^{A3}$, -$L^A$-$R^{A4}$, or -$L^A$-$R^{A5}$;
wherein:
  each —$R^{A1}$ is independently saturated aliphatic $C_{1-6}$alkyl;
  each —$R^{A2}$ is independently saturated $C_{3-6}$cycloalkyl;
  each —$R^{A3}$ is independently non-aromatic $C_{3-8}$heterocyclyl;
  each —$R^{A4}$ is independently $C_{6-10}$carboaryl;
  each —$R^{A5}$ is independently $C_{6-10}$heteroaryl;
  each -$L^A$- is independently saturated aliphatic $C_{1-3}$alkylene;
and wherein:
each $C_{1-6}$alkyl, $C_{3-6}$cycloalkyl, non-aromatic $C_{3-8}$heterocyclyl, $C_{6-10}$carboaryl, $C_{6-10}$heteroaryl, and $C_{1-3}$alkylene is optionally substituted, for example, with one or more substituents;
each —$P^A$ is independently selected from:
  —$R^B$,
  —$OR^B$, -$L^L$-$OR^B$,
  —F, —Cl, —Br, —I,
  —$CF_3$, —$OCF_3$,
  —$NO_2$,
  —$NR^B_2$, —$NR^{BB}R^{BC}$,
  -$L^L$-$NR^B_2$, -$L^L$-$NR^{BB}R^{BC}$;
and each -$L^L$- is independently saturated aliphatic $C_{1-6}$alkylene;
each —$R^B$ is independently:
  —$R^{B1}$, —$R^{B2}$, —$R^{B3}$, —$R^{B4}$, —$R^{B5}$,
  -$L^B$-$R^{B2}$, -$L^B$-$R^{B3}$, -$L^B$-$R^{B4}$, or -$L^B$-$R^{B5}$;
wherein:
  each —$R^{B1}$ is independently saturated aliphatic $C_{1-6}$alkyl;
  each —$R^{B2}$ is independently saturated $C_{3-6}$cycloalkyl;
  each —$R^{B3}$ is independently non-aromatic $C_{3-8}$heterocyclyl;
  each —$R^{B4}$ is independently $C_{6-10}$carboaryl;
  each —$R^{B5}$ is independently $C_{6-10}$heteroaryl;
  each -$L^B$- is independently saturated aliphatic $C_{1-3}$alkylene;
in each group —$NR^{BB}R^{BC}$, $R^{BB}$ and $R^{BC}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O;
and the dashed line indicates that the bond is a single bond or a double bond between the 4a and 9a atoms.

In other aspects of the invention there are provided methods for the synthesis of intermediate compounds for use in the synthesis of compound (I).

The invention also provides the use of the intermediate compounds in the synthesis of compound (I). The invention also provides the use of the intermediate compounds in the synthesis of other intermediate compounds.

Thus, in one aspect of the invention there are provided methods for the synthesis of compounds of formula (II):

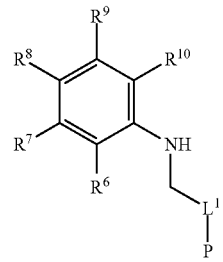
(II)

wherein —$R^6$, —$R^7$, —$R^8$, —$R^9$, -$L^1$-, and —P are as defined according to compound (I), and —$R^{19}$ is independently —H or —$P^A$.

Thus, in another aspect of the invention there are provided methods for the synthesis of compounds of formula (IV):

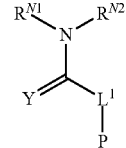
(IV)

wherein -$L^1$- and —P are as defined according to compound (II);
Y is S or O; and
—$R^{N1}$ and —$R^{N2}$ are each independently —H or saturated $C_{1-6}$alkyl, or —$R^{N1}$ and —$R^{N2}$ taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S.

In another aspect of the invention there are provided methods for the synthesis of compounds of formula (V):

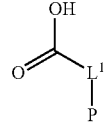
(V)

wherein -$L^1$- and —P are as defined according to compound (II).

Thus, in another aspect of the invention there are provided methods for the synthesis of compounds of formula (VI):

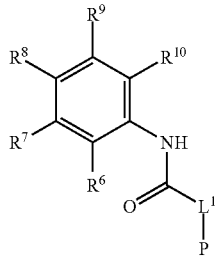

(VI)

wherein —$R^6$, —$R^7$, —$R^8$, —$R^9$, —$R^{10}$, -$L^1$-, and —P are as defined according to compound (II).

In other aspects of the invention there are provided methods for the synthesis of compounds of formula (VIII) and (IX):

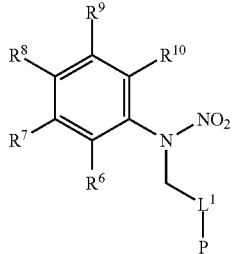

(VIII)

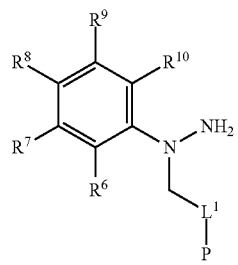

(IX)

wherein —$R^6$, —$R^7$, —$R^8$, —$R^9$, —$R^{10}$, -$L^1$-, and —P are as defined according to compound (II).

Preparation of Compound (II)

In one aspect the present invention provides a method for the synthesis of a compound of formula (II). The method comprises one or more steps selected from:

(i) the step of converting compound (III) to compound (IV) as described below in Step 1;
(ii) the step of converting compound (IV) to compound (V) as described below in Step 2;
(iii) the step of converting compound (V) to compound (VI) as described below in Step 3; and
(iv) the step of converting compound (VI) to compound (II) as described below in Step 4.

In one embodiment, the method comprises at least step (iv).
In one embodiment, the method comprises at least step (i).
In one embodiment, the method comprises the steps of, in order, (iii) and (iv).
In one embodiment, the method comprises the steps of, in order, (ii), (iii) and (iv).
In one embodiment, the method comprises the steps of, in order, (i), (ii), (iii) and (iv).

In other aspects of the invention, there is provided the use of a compound of formula (III), the use of a compound of formula (IV), the use of a compound of formula (V), or the use of a compound of formula (VI) in the synthesis of a compound of formula (VI).

Step 1

In one embodiment, the method comprises the step of reacting a compound of formula (III) to form a compound of formula (IV):

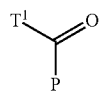

(III)

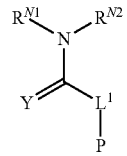

(IV)

wherein, for compounds of formula (III), —P is as defined according to the compounds of formula (II) and -$T^1$ is independently linear saturated $C_{1-6}$ alkyl. Compound (IV) is as defined above.

In one embodiment, compound (III) is reacted with an amine, $NHR^{N1}R^{N2}$, and a sulfinating agent to form compound (IV), where —$R^{N1}$ and —$R^{N2}$ are as defined according to the compounds of formula (IV).

In this embodiment, the reaction may be referred to as a Kindler thionation.

In one embodiment, the product of the reaction is a thioamide i.e. Y is S.

In one embodiment, the product of the reaction is an amide i.e. Y is O.

In one embodiment, the product of the reaction is a mixture of amide and thioamide.

In one embodiment, the thioamide product is obtained where one of —$R^{N1}$ and —$R^{N2}$ is other than —H.

In one embodiment, the amide product is obtained where —$R^{N1}$ and —$R^{N2}$ are each —H.

In one embodiment, the amide product is obtained via the corresponding thioamide.

In one embodiment, the amine has a low boiling point. A reaction mixture comprising a low boiling amine requires less heat to bring to reflux compared to a high boiling amine.

In one embodiment, the amine has a boiling point of 130° C. or less.

In one embodiment, the amine has a boiling point of 100° C. or less.

In one embodiment, the amine has a boiling point of 80° C. or less.

In one embodiment, the amine has a boiling point of 60° C. or less.

In one embodiment, the amine has a boiling point of 40° C. or less.

In one embodiment, the reaction mixture is heated to reflux.

In one embodiment, the reaction is performed at a temperature of 10 to 170° C.

In one embodiment, the reaction is performed at a temperature of 30 to 160° C.

In one embodiment, the reaction is performed at a temperature of 10 to 140° C.

In one embodiment, the reaction is performed at a temperature of 30 to 140° C.

In one embodiment, the reaction is performed at a temperature of 30 to 80° C.

In one embodiment, the reaction is performed at a temperature of 30 to 60° C.

In one embodiment, the reaction is performed for a time of at least 5 hours.

In one embodiment, the reaction is performed for a time of at least 10 hours.

In one embodiment, the reaction is performed for a time of at least 15 hours.

In one embodiment, the reaction is performed for a time of about 16 hours.

In one embodiment, the reaction is performed in a sealed reaction vessel.

In one embodiment, the reaction is performed in the presence of a tertiary amine base.

In one embodiment, the tertiary amine base is pyridine.

In one embodiment, compound (III) is independently 5-acetyl-2-methylpyridine.

In one embodiment, $NHR^{N1}R^{N2}$ is independently morpholine. In this embodiment, compound (IV) is 6-methyl-3-pyridylthioacetmorpholide.

In one embodiment, $NHR^{N1}R^{N2}$ is independently diethylamine. In this embodiment, compound (IV) is N,N-diethyl-2-(6-methyl-pyridin-3-yl)-thioacetamide.

In one embodiment, $NHR^{N1}R^{N2}$ is independently ammonia. In this embodiment, compound (IV) is 2-(6-methyl-pyridin-3-yl)-acetamide.

In one embodiment, the sulfinating agent is, or comprises, sulfur.

In one embodiment, the sulfinating agent is sulfur.

In one embodiment, the sulfinating agent is, or comprises, a polysulfide salt.

In one embodiment, the sulfinating agent is a polysulfide salt.

In one embodiment, the polysulfide salt is ammonium polysulfide.

In one embodiment, the step of reacting 5-acetyl-2-methylpyridine to form 6-methyl-3-pyridylthioacetmorpholide is performed as described in Sperber et al., which is incorporated by reference herein. In particular, the intermediates in the synthesis of ethyl 6-methyl-3-pyridylacetate are referred to, as described in Table 1 and pages 708-709.

Step 2

In one embodiment, the method comprises the step of reacting a compound of formula (IV) to form a compound of formula (V):

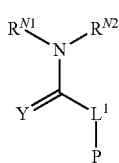

(IV)

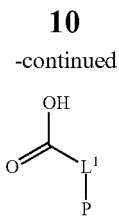

(V)

wherein compounds (IV) and (V) are as defined above. The reaction may be referred to as the hydrolysis of the thioamide or amide, as appropriate.

In one embodiment, the hydrolysis is by reaction with a base.

In one embodiment, the base is or comprises a hydroxide salt.

In one embodiment, the base is or comprises an alkali metal hydroxide.

In one embodiment, the base is or comprises sodium or lithium hydroxide.

In one embodiment, the base is sodium hydroxide.

In one embodiment, the base is an aqueous base.

In one embodiment, the molar ratio of base to compound (IV) is from 2.0 to 4.0.

In one embodiment, the range is 2.5 to 3.5.

In one embodiment, the ratio is about 3.3.

In one embodiment, the base is used in an amount of from 2.0 to 4.0 molar equivalents, relative to the amount of compound (IV).

In one embodiment, the base is used in an amount of from 2.5 to 3.5 molar equivalents, relative to the amount of compound (IV).

In one embodiment, the base is used in an amount of about 3.3 molar equivalents, relative to the amount of compound (IV).

In one embodiment, the reaction is performed in an aqueous medium.

In one embodiment, the aqueous medium comprises a saturated aliphatic $C_{1-6}$ alkyl alcohol.

In one embodiment, the aqueous medium comprises methanol, ethanol or iso-propyl alcohol.

In one embodiment, the aqueous medium comprises ethanol.

In one embodiment, the reaction is performed at reflux.

In one embodiment, the reaction is performed at a temperature of 10 to 100° C.

In one embodiment, the reaction is performed at a temperature of 30 to 90° C.

In one embodiment, the reaction is performed at a temperature of 50 to 85° C.

In one embodiment, the reaction is performed for a time of at least 5 hours.

In one embodiment, the reaction is performed for a time of at least 10 hours.

In one embodiment, the reaction is performed for a time of at least 15 hours.

In one embodiment, the reaction is performed for a time of about 16 hours.

In one embodiment, the reaction is stirred during the reaction step.

In one embodiment, after reaction, the aqueous medium is concentrated.

In one embodiment, after reaction, the aqueous medium is concentrated by removal of the saturated aliphatic $C_{1-6}$ alkyl alcohol, where present.

In one embodiment, after reaction, the aqueous medium is neutralised.

In one embodiment, after reaction, the pH of the aqueous medium is adjusted to lower pH.

In one embodiment, the lower pH is 6-8.

In one embodiment, the lower pH is about 7.

In one embodiment, the lower pH is 7.0.

In one embodiment, the pH of the aqueous medium is adjusted with aqueous acid.

In one embodiment, the pH of the aqueous medium is adjusted with aqueous hydrochloric acid.

In one embodiment, after reaction, the pH of the aqueous medium is adjusted after the aqueous medium is concentrated.

In one embodiment, after reaction, the aqueous medium is removed. The product is retained in the remaining mixture.

In one embodiment, after reaction, the aqueous medium is removed after the pH of the aqueous medium is adjusted.

In one embodiment, after the aqueous medium is removed, the remaining mixture is slurried in solvent.

In one embodiment, the solvent is or comprises a saturated aliphatic $C_{1-6}$ alkyl alcohol.

In one embodiment, the solvent is or comprises methanol, ethanol or iso-propyl alcohol.

In one embodiment, the solvent is methanol.

In one embodiment, the solvent is hot.

In one embodiment, the solvent is at a temperature of 20 to 60° C.

In one embodiment, the solvent is at a temperature of 30 to 55° C.

In one embodiment, the solvent is at a temperature of 40 to 50° C.

In one embodiment, after the remaining mixture is slurried in solvent, the slurry is filtered, and the filtrate collected.

In one embodiment, the slurry is filtered hot.

In one embodiment, the slurry is at a temperature of 20 to 60° C.

In one embodiment, the slurry is at a temperature of 30 to 55° C.

In one embodiment, the slurry is at a temperature of 40 to 50° C.

In one embodiment, after filtration, the filtrate is concentrated.

In one embodiment, after filtration, the filtrate is purified by chromatography.

In one embodiment, the filtrate is concentrated filtrate.

In one embodiment, the chromatography is flash column chromatography.

In one embodiment, the eluant in the chromatography is a mixture of ethyl acetate and methanol.

In one embodiment, the eluant is a 9:1 mixture of ethyl acetate and methanol.

Hydrolysis of compound (IV) produces an amine, $NHR^{N1}R^{N2}$, as a reaction by-product, where and —$R^{N1}$ and —$R^{N2}$ are as defined for compound (IV).

In one embodiment, after reaction, the amine by-product is separated from compound (V).

The amine by-product may be separated from compound (V) during concentration of the aqueous medium, or subsequently during concentration of the filtrate.

In one embodiment, the amine by-product is a low boiling amine.

In one embodiment, the amine by-product has a boiling point of 100° C. or less.

In one embodiment, the amine by-product has a boiling point of 80° C. or less.

In one embodiment, the amine by-product has a boiling point of 60° C. or less.

In one embodiment, the amine by-product has a boiling point of 40° C. or less.

In one embodiment, the amine by-product is separated from compound (V) by distillation, which includes concentration in vacuo.

Where the amine by-product is a high boiling amine, the separation of the by-product from compound (V) may be difficult by concentration alone. In one embodiment, a high boiling amine by-product is separated from compound (V) by chromatography, or distillation and chromatography.

In one embodiment, after reaction, the amine by-product is separated from the aqueous medium by washing with an organic solvent.

In one embodiment, after reaction, the aqueous medium is washed with an organic solvent.

In one embodiment, after reaction, the aqueous medium is washed with an organic solvent after concentration of the aqueous medium.

In one embodiment, the aqueous medium is washed once, twice, or three times with the organic solvent.

In one embodiment, the aqueous medium is washed three times with the organic solvent.

In one embodiment, the organic solvent is dichloromethane (DCM).

In one embodiment, the amine by-product is diethylamine.

In one embodiment, the amine by-product is ammonia.

In one embodiment, the amine by-product is morpholine.

In one embodiment, compound (IV) is independently 6-methyl-3-pyridylthioacetmorpholide.

In one embodiment, compound (IV) is independently N,N-diethyl-2-(6-methyl-pyridin-3-yl)-thioacetamide.

In one embodiment, compound (IV) is independently 2-(6-methyl-pyridin-3-yl)-acetamide In one embodiment, compound (V) is independently 6-methyl-3-pyridineacetic acid.

In one embodiment, the step of reacting 6-methyl-3-pyridylthioacetmorpholide to form 6-methyl-3-pyridineacetic acid is performed as described in Sperber et al., which is incorporated by reference herein. In particular, the intermediates in the synthesis of ethyl 6-methyl-3-pyridylacetate are referred to, as described in Table 1 and pages 708-709.

Step 3

In one embodiment, the method comprises the step of reacting a compound of formula (V) to form a compound of formula (VI):

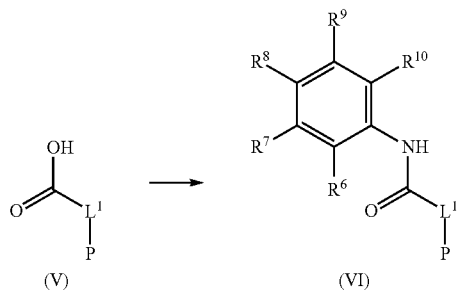

wherein compounds (V) and (VI) are as defined above.

In one embodiment, compound (V) is reacted with a compound of formula (VII) to form compound (VI):

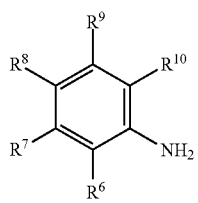

(VII)

wherein —R⁶, —R⁷, —R⁸, —R⁹, and —R¹⁹ are as defined according to the compounds of formula (II).

The reaction may be referred to as the coupling of compounds (V) and (VII).

In one embodiment, the molar ratio of compound (V) to compound (VII) is 1.0 to 3.0.

In one embodiment, the molar ratio of compound (V) to compound (VII) is 1.1 to 2.0.

In one embodiment, the ratio is about 1.5.

In one embodiment, the amine compound (VII) is used in an amount of from 1.0 to 3.0 molar equivalents, relative to the amount of carboxylic acid compound (V).

In one embodiment, the amine compound (VII) is used in an amount of from 1.1 to 2.0 molar equivalents, relative to the amount of carboxylic acid compound (V).

In one embodiment, the amine compound (VII) is used in an amount of about 1.5 molar equivalents, relative to the amount of carboxylic acid compound (V).

In one embodiment, the reaction is performed in an organic medium.

In one embodiment, the organic medium is or comprises an ether solvent.

In one embodiment, the ether solvent is tetrahydrofuran (THF).

In one embodiment, the organic medium is or comprises DCM.

In one embodiment, the organic medium is or comprises dimethylformamide (DMF).

In one embodiment, the organic medium is anhydrous DMF.

In one embodiment, the reaction is performed in the presence of a phase transfer catalyst (PTC).

Phase transfer catalysts are known in the art, and include quaternary ammonium salts and phosphonium salts. Examples of ammonium salts include, but are not limited to, tetraalkylammonium salts (e.g. Bu₄NI, Bu₄NBF₄, Bu₄NBr, Bu₄NF), quaternary pyridinium salts, and other phase transfer agents commonly used in the domestic chemicals market, such as cetyl trimethylammonium bromide, cocamidopropyl betaine. Examples of phosphonium salts include, but are not limited to alkyl and aryl phosphonium halides (e.g. tetraphenyl phosphonium bromide, methyl triphenyl phosphonium bromide, butyl triphenyl phosphonium chloride, tetradecyl (trihexyl)phosphonium chloride, tetradecyl(trihexyl)phosphonium bromide).

Other phase transfer catalysts of use in the methods of the invention include those discussed in *Aldrichimica Acta,* 1976, volume 9, issue 3 and in the chapter on PTC in "Industrial Catalysis" by Jens Hagen (Wiley-VCH, 2006), which are each incorporated herein by reference.

In one embodiment the PTC is used in an amount of from 5 to 25 mol %, relative to the amount of compound (V).

In one embodiment the PTC is used in an amount of from 5 to 15 mol %, relative to the amount of compound (V).

In one embodiment the PTC is used in an amount of about 10 mol %, relative to the amount of compound (V).

In one embodiment the PTC is Bu₄NI.

In one embodiment the PTC is Bu₄NBF₄.

In one embodiment, the reaction, is performed under an inert atmosphere.

In one embodiment, the reaction is performed under an argon or nitrogen atmosphere.

In one embodiment, the reaction is stirred during the reaction step.

In one embodiment, compound (V) is coupled to compound (VII) using one or more coupling reagents.

In one embodiment, compound (V) is coupled to compound (VII) using a coupling reagent.

In one embodiment, the coupling reagent is a carbodiimide.

In one embodiment, the coupling reagent is a haloformate.

In one embodiment, the coupling reagent is or comprises hydroxybenzotriazole (HOBt), dimethylaminopyridine (DMAP), benzotriazol-1-yl-oxytripyrrolidinophosphonium hexafluorophosphate (PyBOP), 1-(mesitylene-2-sulfonyl)-3-nitro-1,2,4-triazole (MSNT), 2-(1H-7-azabenzotriazol-1-yl)-1,1,3,3-tetramethyluronium hexafluorophosphate (HATU), O-Benzotriazole-N,N,N',N'-tetramethyluronium hexafluorophosphate (HBTU), 2-(6-chloro-1-H-benzotriazole-1-yl)-1,1,3,3-tetramethylaminium hexafluorophosphate (HCTU), bromo-tris-pyrrolidino phosphoniumhexafluorophosphate (PyBroP), or N,N,N',N'-tetramethyl-O-(benzotriazol-1-Muronium tetrafluoroborate (TBTU).

Other coupling reagents suitable for use in the reaction include those condensation reagents described in the Novabiochem Catalog 2006/2007, and in particular at pages 337-347 and Sections 3.1-3.2.

In one embodiment, the coupling reagent is added before compound (VII) is added.

In one embodiment, the coupling reagent is added after compound (VII) is added.

In one embodiment, the coupling reagent is added at the same time as compound (VII) is added.

In one embodiment, the molar ratio of compound (V) to the coupling reagent is 1.0 to 2.0.

In one embodiment, the molar ratio of compound (V) to the coupling reagent is 1.0 to 1.5.

In one embodiment, the ratio is about 1.1.

In one embodiment, the coupling reagent is used in an amount of from 1.0 to 3.0 molar equivalents, relative to the amount of carboxylic acid compound (V).

In one embodiment, the coupling reagent is used in an amount of from 1.5 to 2.5 molar equivalents, relative to the amount of carboxylic acid compound (V).

In one embodiment, the coupling reagent is used in an amount of about 2.0 molar equivalents, relative to the amount of carboxylic acid compound (V).

In one embodiment, the coupling reagent is used in an amount of from 1.0 to 1.5 molar equivalents, relative to the amount of carboxylic acid compound (V).

In one embodiment, the coupling reagent is used in an amount of about 1.1 molar equivalents, relative to the amount of carboxylic acid compound (V).

In one embodiment, the coupling reagent is used in combination with a base.

In one embodiment, the base is an organic base.

In one embodiment, the organic base is an amine base.

In one embodiment, the amine base is triethylamine, di-iso-propylethylamine or N-methylmorpholine.

In one embodiment, the molar ratio of compound (V) to the base is 1.0 to 2.0.

In one embodiment, the molar ratio of compound (V) to the coupling reagent is 1.0 to 1.2.

In one embodiment, the ratio is about 1.0.

In one embodiment, the base is used in an amount of from 1.0 to 2.0 molar equivalents, relative to the amount of carboxylic acid compound (V).

In one embodiment, the base is used in an amount of from 1.0 to 2.0 molar equivalents, relative to the amount of carboxylic acid compound (V).

In one embodiment, the base is used in an amount of about 1.0 molar equivalents, relative to the amount of carboxylic acid compound (V).

In one embodiment, after filtration, the filtrate is purified by chromatography.

In one embodiment, the chromatography is flash column chromatography.

In one embodiment, the eluant in the chromatography is or comprises ethyl acetate.

Carbodiimide Coupling Reaction:

In one embodiment, the coupling reagent is a carbodiimide.

In one embodiment, the carbodiimide is N,N'-dicyclohexylcarbodiimide (DCC), 1-ethyl-3-(3-dimethylaminopropyl)carbodiimide (EDC), or N,N'-diisopropylcarbodiimide DIC.

In one embodiment, the carbodiimide is used in combination with one or more of HOBt, DMAP, PyBOP, MSNT, HATU, HBTU, HCTU, PyBroP, or TBTU.

In one embodiment, the reaction is performed at room temperature.

In one embodiment, the reaction is performed at a temperature of 10 to 30° C.

In one embodiment, the reaction is performed at a temperature of 15 to 25° C.

In one embodiment, the reaction is performed for a time of 2 to 12 hours.

In one embodiment, the reaction is performed for a time of 4 to 10 hours.

In one embodiment, the reaction is performed for about 6 hours.

In one embodiment, after reaction, the organic medium is filtered, and the filtrate collected.

In one embodiment, after filtration, the filtrate is concentrated.

In one embodiment, after filtration, the filtrate is purified by chromatography.

In one embodiment, the filtrate is a concentrated filtrate.

In one embodiment, the chromatography is flash column chromatography.

In one embodiment, the eluant in the chromatography is or comprises ethyl acetate.

Mixed Anhydride Coupling Reaction:

In one embodiment, the coupling reagent is a haloformate.

In one embodiment, the haloformate is a $C_{1-6}$ alkyl haloformate.

In one embodiment, the haloformate is butyl chloroformate.

In one embodiment, the haloformate is iso-butyl chloroformate.

In one embodiment, the reaction is performed for a time of 2 to 24 hours.

In one embodiment, the reaction is performed for a time of 4 to 18 hours.

In one embodiment, the reaction is performed for about 16 hours.

In one embodiment, the reaction is performed at room temperature or less.

In one embodiment, the room temperature is 25° C.

In one embodiment, the room temperature is a temperature of 10 to 30° C.

In one embodiment, the room temperature is a temperature of 15 to 25° C.

In one embodiment, the coupling reagent is added to compound (V) at a temperature less than room temperature.

In one embodiment, less than room temperature is 0° C. or less.

In one embodiment, less than room temperature is −10° C. or less.

In one embodiment, less than room temperature is −78° C.

In one embodiment, after the coupling reagent is added to compound (V) at a temperature less than room temperature, the reaction is allowed to warm to room temperature.

In one embodiment, the reaction is held at a temperature less than room temperature for at most 60 min, and then allowed to warm to room temperature.

In one embodiment, the reaction is held at a temperature less than room temperature for at most 30 min.

In one embodiment, the reaction is cooled using a −78° C. coolant bath.

In one embodiment, the reaction is cooled, to produce an internal temperature of the reaction mixture of between −50° C. and −25° C.

In one embodiment, the reaction is cooled to produce an internal temperature of the reaction mixture of between −45° C. and −35° C.

In one embodiment, the reaction is cooled to produce an internal temperature of the reaction mixture of about −40° C.

Step 4

In one embodiment, the method comprises the step of reacting a compound of formula (VI) to form a compound of formula (II):

wherein compounds (VI) and (II) are as defined above. The reaction may be referred to as the reduction of the amide.

In one embodiment, compound (VI) is reacted with a reducing agent to form compound (II).

In one embodiment, the reducing agent is, or comprises, $LiAlH_4$.

In one embodiment, the reducing agent is $LiAlH_4$.

In one embodiment, the reducing agent is, or comprises, a borane reducing agent.

In one embodiment, the reducing agent is a borane reducing agent.

In one embodiment, the borane reducing agent is $BH_3$ or a $C_{3-10}$ dialkyl borane.

In one embodiment, the $C_{3-10}$ dialkyl borane is 9-borabicyclo(3.3.1)nonane (9-BBN) or bis-3-methyl-2-butylborane.

In one embodiment, the reducing agent is, or comprises, a borohydride.

In one embodiment, the borohydride is $Bu_4NBH_4$.

In one embodiment, the molar ratio of compound (VI) to the reducing reagent is 1.0 to 10.0.

In one embodiment, the molar ratio of compound (VI) to the reducing reagent is 2.0 to 7.5.

In one embodiment, the ratio is about 5.0.

In one embodiment, the reducing agent is used in an amount of from 1.0 to 10.0 molar equivalents, relative to the amount of compound (VI).

In one embodiment, the reducing agent is used in an amount of from 2.0 to 7.5 molar equivalents, relative to the amount of compound (VI).

In one embodiment, the reducing agent is used in an amount of about 5.0 molar equivalents, relative to the amount of compound (VI).

In one embodiment, the reducing agent is used in an amount of about 3.0 molar equivalents, relative to the amount of compound (VI).

In one embodiment, the reaction is performed in an organic medium.

In one embodiment, the organic medium is or comprises an ether solvent.

In one embodiment, the ether solvent is THF.

In one embodiment, the organic medium is DCM.

In one embodiment, the concentration of compound (VI) in the organic medium is at least 0.1 M.

In one embodiment, the concentration of compound (VI) in the organic medium is at least 0.2 M.

In one embodiment, the concentration of compound (VI) in the organic medium is at least 0.4 M.

In one embodiment, the concentration of compound (VI) in the organic medium is about 0.4 M.

In one embodiment, the reaction is performed at reflux.

In one embodiment, the reaction is performed at a temperature of 10 to 100° C.

In one embodiment, the reaction is performed at a temperature of 30 to 90° C.

In one embodiment, the reaction is performed at a temperature of 50 to 85° C.

In one embodiment, the reaction is performed for 5 to 40 hours.

In one embodiment, the reaction is performed for 10 to 20 hours.

In one embodiment, the reaction is performed for 20 hours at most.

In one embodiment, the reaction is performed for a time of about 16 hours.

In one embodiment, the reaction is stirred during the reaction step.

In one embodiment, the reducing reagent is added to compound (VI) at a temperature less than room temperature.

In one embodiment, less than room temperature is 0° C. or less.

In one embodiment, less than room temperature is −10° C. or less.

In one embodiment, less than room temperature is −78° C.

In one embodiment, less than room temperature is about 0° C.

In one embodiment, after the reducing reagent is added to compound (VI) at a temperature less than room temperature, the reaction is allowed to warm to room temperature.

In one embodiment, the reaction is held at a temperature less than room temperature for at most 30 min, and then allowed to warm to room temperature.

In one embodiment, the reaction is held at a temperature less than room temperature for at most 10 min.

In one embodiment, the reducing reagent is added to compound (VI) portionwise until no further gas evolution is observed. Thereafter the remaining reducing agent may be added in one portion.

In one embodiment, the reaction is terminated by the addition of wet organic solvent.

In one embodiment, the organic solvent is an ether solvent.

In one embodiment, the ether solvent is THF.

In one embodiment, the wet organic solvent is added until no further gas evolution is observed.

In one embodiment, after reaction, the reaction mixture is concentrated.

In one embodiment, after reaction, the reaction mixture is concentrated to remove the organic solvent.

In one embodiment, after reaction, the reaction mixture is hydrolysed.

In one embodiment, after reaction, the reaction mixture is hydrolysed by boiling in aqueous acid.

In one embodiment, the aqueous acid is aqueous hydrochloric acid solution.

In one embodiment, the aqueous hydrochloric acid solution is at a concentration of 0.5M to 2.0M.

In one embodiment, the hydrochloric acid solution is at a concentration of about 1.0M.

In one embodiment the hydrolysis is performed for 10 to 60 minutes.

In one embodiment the hydrolysis is performed for about 30 minutes.

In one embodiment the hydrolysis is performed after the reaction mixture is concentrated.

In one embodiment, after reaction, the reaction mixture is filtered, and the filtrate collected.

In one embodiment, the collected solids are washed with organic solvent. The washings are combined with the collected filtrate.

In one embodiment, the organic solvent is an ether solvent as describe above.

In one embodiment, after filtration, the filtrate is dried with a drying agent.

In one embodiment, the drying agent is magnesium sulfate or sodium sulfate.

In one embodiment, after filtration, the organic medium is removed e.g. in vacuo. The product is retained in the remaining mixture.

In one embodiment, after filtration, the filtrate is purified by chromatography.

In one embodiment, the filtrate is concentrated filtrate.

In one embodiment, the chromatography is flash column chromatography.

In one embodiment, the eluant in the chromatography is a mixture of ethyl acetate and petrol.

In one embodiment, the eluant is a 1:1 mixture of ethyl acetate and petrol.

In one embodiment, the eluant is a 1:1 mixture of ethyl acetate and petrol (40-60).

Preferred Synthesis

In one embodiment, the compound of formula (II) is [2-(6-methyl-pyridin-3-yl)-ethyl]-p-tolyl-amine 1) and is prepared from 3-acetyl-6-methylpyridine as shown in scheme 1.

Scheme 1.

In an alternative embodiment, N,N-diethyl-2-(6-methyl-pyridin-3-yl)-thioacetamide (10) is used in place of 6-methyl-3-pyridylthioacetmorpholide (9) in the scheme above.

In an alternative embodiment, 2-(6-methyl-pyridin-3-yl)-acetamide (14) is used in place of 6-methyl-3-pyridylthioacetmorpholide (9) in the scheme above.

Preparation of Compound (VI)

In one aspect the present invention provides a method for the synthesis of a compound of formula (VI). The method comprises one or more steps selected from:
  (i) the step of converting a compound of formula (III) to compound (IV) as described above in Step 1;
  (ii) the step of converting a compound of formula (IV) to compound (V) as described above in Step 2; and
  (iii) the step of converting a compound of formula (V) to compound (VI) as described above in Step 3.

In one embodiment, the method comprises at least step (iii).

In one embodiment, the method comprises the steps of, in order, (ii) and (iii).

In one embodiment, the method comprises the steps of, in order, (i), (ii) and (iii).

In other aspects of the invention, there is provided the use of a compound of formula (III), the use of a compound of formula (IV), or the use of a compound of formula (V) in the synthesis of a compound of formula (VI).

Preparation of Compound (V)

In one aspect the present invention provides a method for the synthesis of a compound of formula (V). The method comprises one or more steps selected from:
  (i) the step of converting a compound of formula (III) to compound (IV) as described above in Step 1; and
  (ii) the step of converting a compound of formula (IV) to compound (V) as described above in Step 2.

In one embodiment, the method comprises at least step (i).

In one embodiment, the method comprises the steps of, in order, (i) and (ii).

In other aspects of the invention, there is provided the use of a compound of formula (III) or the use of a compound of formula (IV) in the synthesis of a compound of formula (V).

Preparation of Compound (IV)

In one aspect the present invention provides a method for the synthesis of a compound of formula (IV). The method comprises the step of converting a compound of formula (III) to compound (IV) as described above in Step 1.

In another aspect of the invention, there is provided the use of a compound of formula (III) in the synthesis of a compound of formula (IV).

Preparation of Compounds (VIII) and (IX)

In one aspect the present invention provides a method for the synthesis of a compound of formula (VIII).

The method comprises one or more steps selected from:
  (i) the step of converting a compound of formula (III) to compound (IV) as described above in Step 1;
  (ii) the step of converting a compound of formula (IV) to compound (V) as described above in Step 2;
  (iii) the step of converting a compound of formula (V) to compound (VI) as described above in Step 3;
  (iv) the step of converting compound (VI) to compound (II) as described above in Step 4; and optionally the step of:
  (vi) converting compound (II) to compound (VIII).

Step (vi) may be referred to as a nitration reaction. In one embodiment, the nitration is by reaction with a nitrous acid. Compound (II) may be converted to compound (VIII) by the methods described in U.S. Pat. No. 3,409,628. See, for example, the synthesis of 2-methyl-5-(N-nitroso-2-p-tolylaminoethyl)pyridine as described in Example 14. Alternative procedures will be familiar to those of skill in the art.

In one embodiment, compound (VIII) is 2-methyl-5-(N-nitroso-2-p-tolylaminoethyl)pyridine.

In one embodiment, the method comprises at least step (iv).

In one embodiment, the method comprises the steps of, in order, at least step (iv) and (vi).

In one embodiment, the method comprises the steps of, in order, at least step (i) and (vi).

In one embodiment, the method comprises the steps of, in order, (iii) and (iv).

In one embodiment, the method comprises the steps of, in order, (iii), (iv) and (vi).

In one embodiment, the method comprises the steps of, in order, (ii), (iii) and (iv).

In one embodiment, the method comprises the steps of, in order, (ii), (iii), (iv) and (vi).

In one embodiment, the method comprises the steps of, in order, (i), (ii), (iii) and (iv).

In one embodiment, the method comprises the steps of, in order, (i), (ii), (iii), (iv) and (vi).

In one aspect the present invention provides a method for the synthesis of a compound of formula (IX).

The method comprises one or more steps selected from:
  (i) the step of converting a compound of formula (III) to compound (IV) as described above in Step 1;
  (ii) the step of converting a compound of formula (IV) to compound (V) as described above in Step 2;
  (iii) the step of converting a compound of formula (V) to compound (VI) as described above in Step 3;
  (iv) the step of converting compound (VI) to compound (II) as described above in Step 4;
and optionally comprises one or both the steps of:

(vi) converting compound (II) to compound (VIII) as described above; and (vii) converting compound (VIII) to compound (IX).

Step (vii) may be referred to as a reduction reaction. In one embodiment, the reduction is by reaction with zinc in the presence of acid. Compound (VIII) may be converted to compound (IX) by the methods described in U.S. Pat. No. 3,409,628. See, for example, the synthesis of 2-methyl-5-(N-amino-2-p-tolylaminoethyl)pyridine as described in Example 14. Alternative procedures will be familiar to those of skill in the art.

In one embodiment, the method comprises at least step (iv).

In one embodiment, the method comprises the steps of, in order, at least step (iv) and (vii).

In one embodiment, the method comprises the steps of, in order, at least step (iv), (vi) and (vii)

In one embodiment, the method comprises the steps of, in order, at least step (i) and (vii).

In one embodiment, the method comprises the steps of, in order, (iii) and (iv).

In one embodiment, the method comprises the steps of, in order, (iii), (iv) and (vii).

In one embodiment, the method comprises the steps of, in order, (ii), (iii) and (iv).

In one embodiment, the method comprises the steps of, in order, (ii), (iii), (iv) and (vii).

In one embodiment, the method comprises the steps of, in order, (i), (ii), (iii) and (iv).

In one embodiment, the method comprises the steps of, in order, (i), (ii), (iii), (iv) and (vii).

In one embodiment, the method comprises the steps of, in order, (i), (ii), (iii), (iv), (vi) and (vii).

In one embodiment, compound (IX) is 2-methyl-5-(N-amino-2-p-tolylaminoethyl)pyridine.

Preparation of Compound (I)

In one aspect of the invention, there is provided a method for the synthesis of compound (I).

In one embodiment, the method comprises one or more of steps 1-4 as described above in relation to compound (I), and optionally may further comprise step 5, as described below. In this embodiment, in steps 3, 4 and 5, —$R^{10}$ is —H.

In one aspect the present invention provides a method for the synthesis of a compound of formula (II). The method comprises one or more steps selected from:

(i) the step of converting compound (III) to compound (IV) as described above in Step 1;

(ii) the step of converting compound (IV) to compound (V) as described above in Step 2;

(iii) the step of converting compound (V) to compound (VI) as described above in Step 3;

(iv) the step of converting compound (VI) to compound (II) as described above in Step 4; and optionally (v) converting compound (II) to compound (I) as described below in Step 5.

In one embodiment, the method comprises at least step (iv).

In one embodiment, the method comprises the steps of, in order, at least step (iv) and (v).

In one embodiment, the method comprises the steps of, in order, at least step (i) and (v).

In one embodiment, the method comprises the steps of, in order, (iii) and (iv).

In one embodiment, the method comprises the steps of, in order, (iii), (iv) and (v).

In one embodiment, the method comprises the steps of, in order, (ii), (iii) and (iv).

In one embodiment, the method comprises the steps of, in order, (ii), (iii), (iv) and (v).

In one embodiment, the method comprises the steps of, in order, (i), (ii), (iii) and (iv).

In one embodiment, the method comprises the steps of, in order, (i), (ii), (iii), (iv) and (v).

Step 5

In one embodiment, the method further comprises the step of converting a compound of formula (II) to a compound of formula (VIII). The reaction may be referred to as a nitration reaction. In one embodiment, the nitration is by reaction with a nitrous acid. Compound (II) may be converted to compound (VIII) by the methods described in U.S. Pat. No. 3,409,628. See, for example, the synthesis of 2-methyl-5-(N-nitroso-2-p-tolylaminoethyl)pyridine as described in Example 14.

In one embodiment, the method further comprises the step of converting a compound of formula (VIII) to a compound of formula (IX). The reaction may be referred to as a reduction reaction. In one embodiment, the reduction is by reaction with a reducing agent.

In one embodiment, the reduction is by reaction with $LiAlH_4$.

In one embodiment, the reduction is by reaction with $LiAlH_4$ in an ether solvent.

In one embodiment, the ether solvent is THF.

In one embodiment, the reduction is by reaction with zinc.

In one embodiment, the reduction is by reaction with zinc in the presence of acid.

In some embodiment, the use of $LiAlH_4$ over zinc is preferred. On a small scale, the use of zinc in the presence of acid was found to over reduce the substrate to yield the compound of formula (II). The combination of $LiAlH_4$ in THF was found to give compound (IX) in good yield.

Compound (VIII) may be converted to compound (IX) by the methods described in U.S. Pat. No. 3,409,628. See, for example, the synthesis of 2-methyl-5-(N-amino-2-p-tolylaminoethyl)pyridine as described in Example 14.

In one embodiment, method further comprises the steps of, in order, converting a compound of formula (II) to a compound of formula (VIII), and converting a compound of formula (VIII) to a compound of formula (IX).

In one embodiment, the method further comprises the steps of converting a compound of formula (IX) to a compound of formula (I). The reaction may be referred to as a condensation reaction. In one embodiment, the condensation is by reaction with compound (X).

In one embodiment, the method comprises the step of reacting a compound of formula (IX) to form a compound of formula (I).

In one embodiment, the reaction is performed in an organic medium.

In one embodiment, the reaction is performed at reflux.

In one embodiment, the reaction is performed at a temperature of 10 to 100° C.

In one embodiment, the reaction is performed at a temperature of 30 to 90° C.

In one embodiment, the reaction is performed at a temperature of 50 to 85° C.

Compound (IX) may be converted to compound (I) by the methods described in U.S. Pat. No. 3,409,628. See, for example, the synthesis of 2-benzyl-8-methyl-1,3,4,5-tetrahydro-5-[2-(6-methyl-3-pyridyl)ethyl]12H-pyridol[4,3-b]indole as described in Example 14.

In one embodiment, method further comprises the steps of, in order, converting a compound of formula (II) to a compound of formula (VIII); converting a compound of formula (VIII) to a compound of formula (IX); and converting a compound of formula (IX) to a compound of formula (I).

In one embodiment, compound (I) is prepared from compound (II) in a method as described in U.S. Pat. No. 3,409,628, which is incorporated by reference herein. Example methods include Example 14 of that document.

In one embodiment, compound (II) is converted in three steps to compound (I), as shown in Scheme 2.

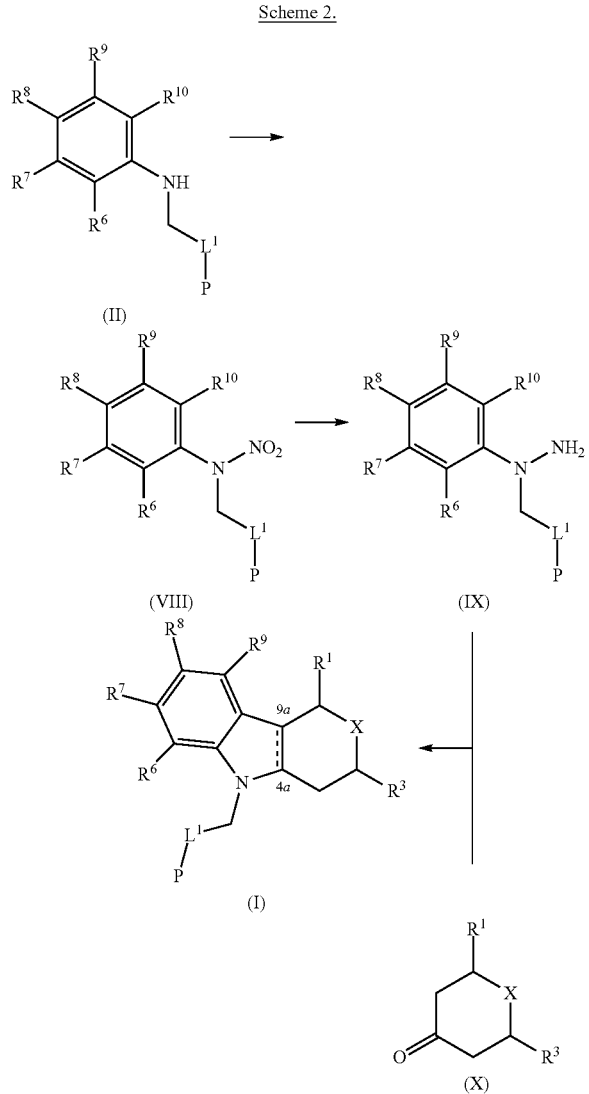

wherein, for compounds (VIII), (IX) and (X), —$R^1$, —$R^3$, —$R^6$, —$R^7$, —$R^8$, —$R^9$, X, -$L^1$-, and —P, are as defined according to compound (II), and —$R^{10}$ is —H.

In one embodiment, compound (I) is dimebon (9-[2-(2'-methyl-5'-pyridyl)ethyl]-3,6-dimethyl-1,2,3,4-tetrahydro-γ-carboline).

In one embodiment, compound (I) is 8-methyl-5-[2-(6-methyl-pyridin-3-yl)-ethyl]-1,3,4,5-tetrahydro-pyrano[4,3-b]indole (15).

In one embodiment, compound (I) is 8-methyl-5-[2-(6-methyl-pyridin-3-yl)-ethyl]-1,3,4,5-tetrahydro-thiopyrano[4,3-b]indole (16).

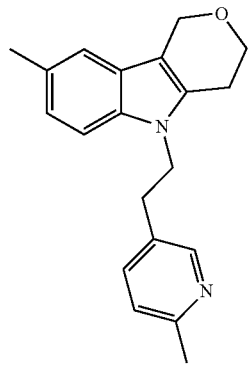

15

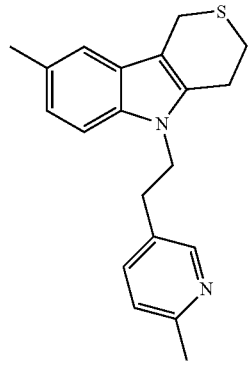

16

In one embodiment, compound (II) is 2-(6-methyl-pyridin-3-yl)-N-p-tolyl-acetamide.

In one embodiment, compound (VIII) is 2-methyl-5-(N-nitroso-2-p-tolylaminoethyl)pyridine.

In one embodiment, compound (IX) is 2-methyl-5-(N-amino-2-p-tolylaminoethyl)pyridine.

In one embodiment, compound (X) is 1-methyl-piperidone-4 (1-methyl-piperidin-4-one).

In one embodiment, compound (X) is tetrahydro-pyran-4-one.

In one embodiment, compound (X) is tetrahydro-thiopyran-4-one.

Use of Compounds as Intermediates

In a general aspect the present invention provides the use of various compounds described herein in the synthesis of other compounds described herein.

Thus, in one aspect, there is provided the use of compound (III) in the synthesis of compound (I) or compound (II).

In another aspect, there is provided the use of compound (IV) in the synthesis of compound (I) or compound (II).

In another aspect, there is provided the use of compound (V) in the synthesis of compound (I) or compound (II).

In another aspect, there is provided the use of compound (VI) in the synthesis of compound (I) or compound (II).

Compounds (III), (IV), (V) and (VI) may be referred to as intermediates in a synthesis of compound (I) or compound (II).

Compounds

In other aspects, the present invention provides compounds of formula (I), (II), (III), (IV), (V), and (VI) as described herein.

In one embodiment, the compound is a compound of formula (VI).

In one embodiment, the compound is a compound of formula (II).

In one embodiment, the compound is a compound of formula (III).

In one embodiment, the compound is a compound of formula (IV).

In one embodiment; the compound is a compound of formula (V).

In one embodiment, the compound is a compound of formula (I).

Embodiments

Various embodiments of the invention are described in detail below.

Preferred Compounds

In one embodiment, the compound of formula (I) is a compound of formula:

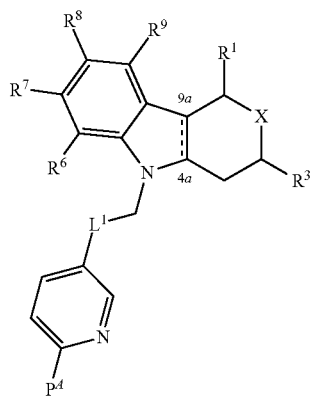

In one embodiment, the compound of formula (I) is a compound of formula:

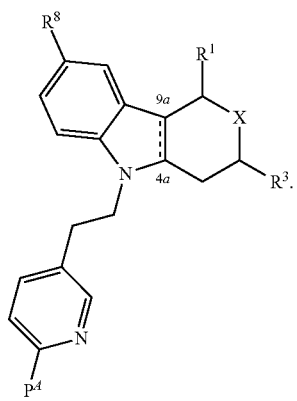

In one embodiment, the compound of formula (I) is dimebon.

In one embodiment, the compound is a compound of formula (I) wherein X is selected from O, S, S(O) and S(O)$_2$.

In one embodiment, the compound of formula (I) is 8-methyl-5-[2-(6-methyl-pyridin-3-yl)-ethyl]-1,3,4,5-tetrahydropyrano[4,3-b]indole.

In one embodiment, the compound of formula (I) is 8-methyl-5-[2-(6-methyl-pyridin-3-yl)-ethyl]-1,3,4,5-tetrahydrothiopyrano[4,3-b]indole.

In one embodiment, the compound of formula (II) is a compound of formula:

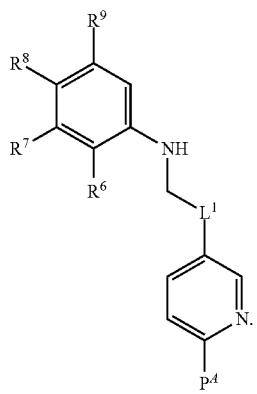

In one embodiment, the compound of formula (II) is a compound of formula:

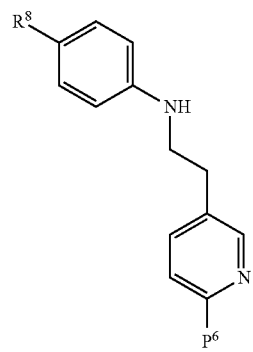

In one embodiment, the compound of formula (II) is:

| Compound | Structure and Name |
|---|---|
| 1 | 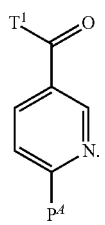<br>[2-(6-methyl-pyridin-3-yl)-ethyl]-p-tolyl-amine |

In one embodiment, the compound of formula (III) is a compound of formula:

(III)

$$\text{[structure]}$$

In one embodiment, the compound of formula (III) is a compound of formula:

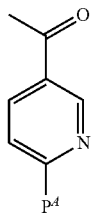
(III)

In one embodiment, the compound of formula (III) is:

| Compound | Structure and Name |
|---|---|
| 8 | 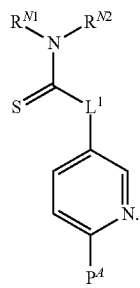<br>3-acetyl-6-methylpyridine |

In one embodiment, the compound of formula (IV) is a compound of formula:

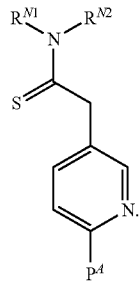
(IV)

In one embodiment, the compound of formula (IV) is a compound of formula:

(IV)

In one embodiment, the compound of formula (IV) is a compound of formula:

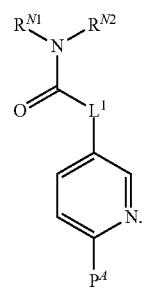
(IV)

In one embodiment, the compound of formula (IV) is a compound of formula:

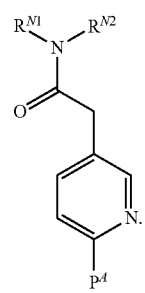
(IV)

In one embodiment, the compound of formula (IV) is selected from:

| Compound | Structure and Name |
|---|---|
| 9 | 6-methyl-3-pyridylthioacetmorpholide |
| 10 | N,N-diethyl-2-(6-methyl-pyridin-3-yl)-thioacetamide |

| Compound | Structure and Name |
|---|---|
| 14 | 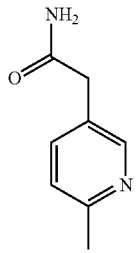<br>2-(6-methyl-pyridin-3-yl)-acetamide |

In one embodiment, the compound of formula (V) is a compound of formula:

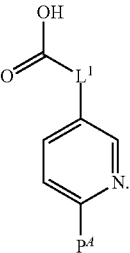

(V)

In one embodiment, the compound of formula (V) is a compound of formula:

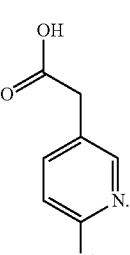

(V)

In one embodiment, the compound of formula (V) is:

| Compound | Structure and Name |
|---|---|
| 11 | 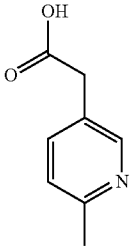<br>6-methyl-3-pyridineacetic acid |

In one embodiment, the compound of formula (VI) is a compound of formula:

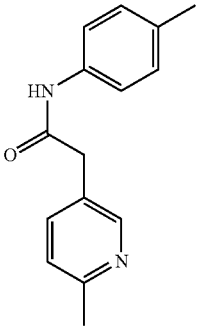

(VI)

In one embodiment, the compound of formula (VI) is a compound of formula:

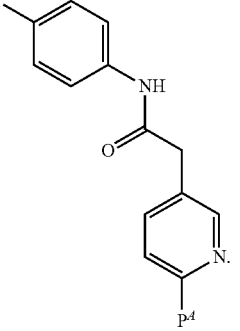

(VI)

In one embodiment, the compound of formula (VI) is:

| Compound | Structure and Name |
|---|---|
| 12 | <br>2-(6-methyl-pyridin-3-yl)-N-p-tolyl-acetamide |

In one embodiment, the compound of formula (VII) is a compound of formula:

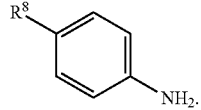
(VII)

In one embodiment, the compound of formula (VII) is:

| Compound | Structure and Name |
|---|---|
| 13 | <br> p-toluidine |

In one embodiment, the compound of formula (VIII) is a compound of formula:

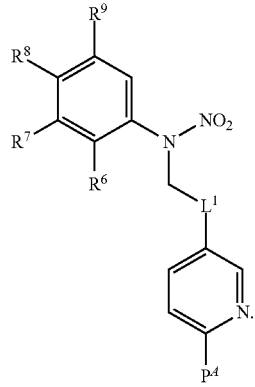
(VII)

In one embodiment, the compound of formula (VIII) is a compound of formula:

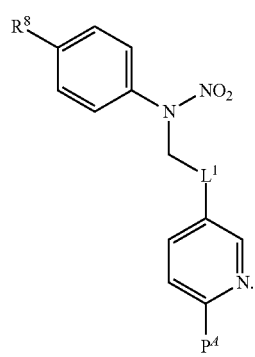
(VII)

In one embodiment, the compound of formula (VIII) is:

| Compound | Structure and Name |
|---|---|
| 4 | 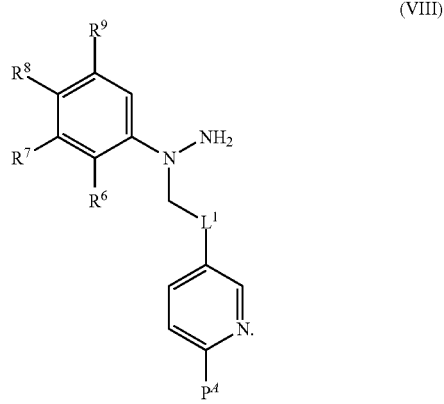 <br> 2-methyl-5-(N-nitroso-2-p-tolylaminoethyl)pyridine |

In one embodiment, the compound of formula (IX) is a compound of formula:

(VIII)

In one embodiment, the compound of formula (IX) is a compound of formula:

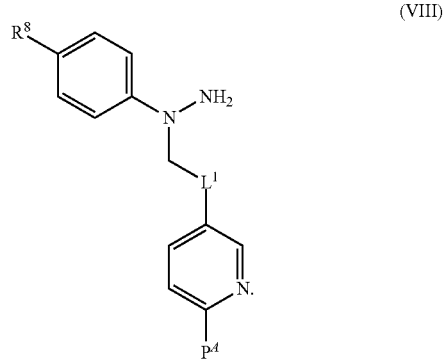
(VIII)

In one embodiment, the compound of formula (IX) is:

| Compound | Structure and Name |
|---|---|
| 5 | 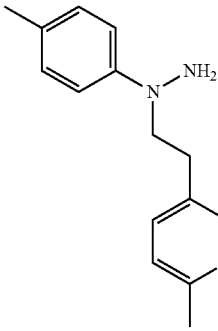<br>2-methyl-5-(N-amino-2-p-tolylaminoethyl)pyridine |

The present invention also includes the salts and solvate forms of the compounds described above.

Preferred Substituents

The embodiments described below apply to each compound described herein where appropriate, unless stated otherwise.

—$R^1$ and —$R^3$

In one embodiment, —$R^1$ is independently —H or —$R^A$.
In one embodiment, —$R^1$ is independently —H.
In one embodiment, —$R^1$ is independently —$R^A$.
In one embodiment, —$R^3$ is independently —H or —$R^A$.
In one embodiment, —$R^3$ is independently —H.
In one embodiment, —$R^3$ is independently —$R^A$.
In one embodiment, —$R^1$ and —$R^3$ are the same.

X

In one embodiment, X is independently selected from $CH_2$, $CHR^A$, $CR^A_2$, NH, $NR^A$, O, S, S(O), and $S(O)_2$.
In one embodiment, X is independently selected from $CH_2$, $CHR^A$, $CR^A_2$, NH, and $NR^A$.
In one embodiment, X is independently selected from $CH_2$, $CHR^A$, and $CR^A_2$.
In one embodiment, X is independently $CH_2$ or $CHR^A$.
In one embodiment, X is independently $CH_2$.
In one embodiment, X is independently $CHR^A$.
In one embodiment, X is independently O, S, S(O) or $S(O)_2$.
In one embodiment, X is independently O or S.
In one embodiment, X is independently NH or $NR^A$.
In one embodiment, X is independently NH.
In one embodiment, X is independently $NR^A$.
In one embodiment, -$L^1$- is independently linear saturated $C_{1-6}$alkylene.
In one embodiment, -$L^1$- is independently linear saturated $C_{1-5}$alkylene.
In one embodiment, -$L^1$- is independently linear saturated $C_{1-3}$alkylene.
In one embodiment, is independently —$CH_2$—.
In one embodiment, is independently —$CH_2CH_2$—.

-$T^1$

In one embodiment, -$T^1$ is independently linear saturated $C_{1-6}$alkyl.
In one embodiment, -$T^1$ is independently linear saturated $C_{1-5}$alkyl.
In one embodiment, -$T^1$ is independently linear saturated $C_{1-3}$alkyl.
In one embodiment, -$T^1$ is independently —$CH_3$.

In one embodiment, -$T^1$ is independently —$CH_2CH_3$.

—$R^6$, —$R^7$, —$R^8$, and —$R^9$

In one embodiment, —$R^6$, —$R^7$, —$R^8$, and —$R^9$ are each independently —H or —$P^A$.
In one embodiment, —$R^6$ is independently —H.
In one embodiment, —$R^6$ is independently —$P^A$.
In one embodiment, —$R^7$ and —$R^9$ are each independently —H.
In one embodiment, —$R^7$ and —$R^9$ are each independently —$P^A$.
In one embodiment, —$R^7$ and —$R^9$ are the same.
In one embodiment, —$R^8$ is independently —H.
In one embodiment, —$R^8$ is independently —$P^A$.
In one embodiment, —$R^6$, —$R^7$, and —$R^9$ are independently —H.
In one embodiment, —$R^6$, —$R^7$, —$R^8$, and —$R^9$ are independently —H.

—$R^{10}$

In one embodiment, —$R^{10}$ is independently —H or —$P^A$.
In one embodiment, —$R^{10}$ is independently —H.
In one embodiment, —$R^{10}$ is independently —$P^A$.
In one embodiment, —$R^{10}$ is the same as —$R^6$.

—P

In one embodiment, —P is independently optionally substituted pyridine or phenyl.
In one embodiment, —P is independently optionally substituted pyridine.
In one embodiment, —P is independently optionally substituted phenyl.
In one embodiment, —P is optionally substituted with one, two, three or four groups —$P^A$.
In one embodiment, —P is phenyl optionally substituted with one, two, three, four or five groups —$P^A$.
In one embodiment, —P is optionally substituted with one group —$P^A$.
In one embodiment, —P is independently:

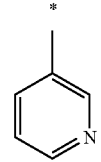

where each of the carbon ring atoms is optionally substituted with a group —$P^A$, and the asterisk indicates the point of attachment.

In one embodiment, —P is independently:

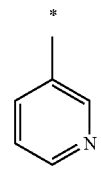

where one of the carbon ring atoms is substituted with a group —$P^A$, and the asterisk indicates the point of attachment.

In one embodiment, —P is independently:

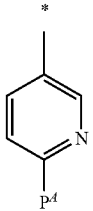

where the asterisk indicates the point of attachment.
In one embodiment, —P is unsubstituted.
—$P^A$
In one embodiment, each —$P^A$, where present, is independently selected from:
—$R^B$,
—$OR^B$, -$L^L$-$OR^B$,
—F, —Cl, —Br, —I,
—$CF_3$, —$OCF_3$,
—$NO_2$,
—$NR^B{}_2$, —$NR^{BB}R^{Bc}$,
-$L^L$-$NR^B{}_2$, -$L^L$-$NR^{BB}R^{Bc}$.
In one embodiment, each —$P^A$, where present, is independently selected from:
—$R^B$,
—$OR^B$, -$L^L$-$OR^B$,
—F, —Cl, —Br, —I,
—$CF_3$, —$OCF_3$,
—$NO_2$.
In one embodiment, each —$P^A$, where present, is independently selected from:
—$R^B$,
—$OR^B$,
—F, —Cl, —Br, —I,
—$CF_3$.
In one embodiment, each —$P^A$, where present, is independently —$R^B$.
In one embodiment, each —$P^A$, where present, is independently —F, —Cl, —Br, or —I.
In one embodiment, each —$P^A$, where present, is independently —$OR^B$.
In one embodiment, each —$P^A$, where present, is independently —$CF_3$.
In one embodiment, each —$P^A$, where present, is independently selected from:
—$NR^B{}_2$, —$NR^{BB}R^{BC}$,
-$L^L$-$NR^B{}_2$, -$L^L$-$NR^{BB}R^{BC}$.
-$L^L$-
In one embodiment, -$L^L$- is independently saturated $C_{1-5}$alkylene.
In one embodiment, -$L^L$- is independently saturated $C_{1-3}$alkylene.
In one embodiment, -$L^L$- is independently —$CH_2$—.
In one embodiment, -$L^L$- is independently —$CH_2CH_2$—.
—$R^A$
In one embodiment, each —$R^{A1}$, where present, is independently:
—$R^{A1}$, —$R^{A2}$, —$R^{A3}$, —$R^{A4}$, —$R^{A5}$,
-$L^A$-$R^{A2}$, -$L^A$-$R^{A3}$, -$L^A$-$R^{A4}$, or -$L^A$-$R^{A5}$.
In one embodiment, each —$R^{A1}$, where present, is independently:
—$R^{A1}$, —$R^{A4}$, —$R^{A5}$,
-$L^A$-$R^{A4}$, or -$L^A$-$R^{A5}$.

In one embodiment each —$R^{A1}$, where present, is independently —$R^{A1}$, —$R^{A4}$, or -$L^A$-$R^{A4}$.
In one embodiment, each —$R^{A1}$, where present, is independently —$R^{A1}$.
—$R^B$
In one embodiment, each —$R^{B1}$, where present, is independently:
—$R^{B1}$, —$R^{B2}$, —$R^{B3}$, —$R^{B4}$, —$R^{B5}$,
-$L^B$-$R^{B2}$, -$L^B$-$R^{B3}$, -$L^B$-$R^{B4}$, or -$L^B$-$R^{B5}$.
In one embodiment, each —$R^{B1}$, where present, is independently:
—$R^{B1}$, —$R^{B4}$, —$R^{B5}$,
-$L^B$-$R^{B4}$, or -$L^B$-$R^{B5}$.
In one embodiment, each —$R^{B1}$, where present, is independently —$R^{B1}$, —$R^{B4}$, or -$L^B$-$R^{B4}$.
In one embodiment, each —$R^{B1}$, where present, is independently —$R^{B1}$.
—$R^{BB}$ and —$R^{BC}$
In one embodiment, —$R^{BB}$ and —$R^{BC}$ taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.
In one embodiment, —$R^{BB}$ and —$R^{BC}$ taken together with the nitrogen atom to which they are attached, form a pyrrolidine, piperazine, piperidine, morpholine, or thiomorpholine ring.
In one embodiment, —$R^{BB}$ and —$R^{BC}$ taken together with the nitrogen atom to which they are attached, form a morpholine or thiomorpholine ring.
In one embodiment, —$R^{BB}$ and —$R^{BS}$ taken together with the nitrogen atom to which they are attached, form a morpholine ring.
—$R^{A1}$ and —$R^{B1}$
In one embodiment, each —$R^{A1}$ or each —$R^{B1}$, where present, is independently saturated aliphatic $C_{1-6}$alkyl.
In one embodiment, each —$R^{A1}$ or each —$R^{B1}$, where present, is independently saturated aliphatic $C_{1-6}$alkyl.
In one embodiment, each —$R^{A1}$ or each —$R^{B1}$, where present, is independently -Me.
In one embodiment, each —$R^{A1}$ or each —$R^{B1}$, where present, is independently -Et.
—$R^{A2}$ and —$R^{B2}$
In one embodiment, each —$R^{A2}$ or each —$R^{B2}$, where present, is independently saturated $C_{3-8}$cycloalkyl.
In one embodiment, each —$R^{A2}$ or each —$R^{B2}$, where present, is independently cyclopropyl.
In one embodiment, each —$R^{A2}$ or each —$R^{B2}$, where present, is independently cyclohexyl.
—$R^{A3}$ and —$R^{B3}$
In one embodiment, each —$R^{A3}$ or each —$R^{B3}$, where present, is independently non-aromatic $C_{3-8}$heterocyclyl.
In one embodiment, each —$R^{A3}$ or each —$R^{B3}$, if present, is a $C_{3-8}$heterocyclyl group that is a 4-, 5-, 6-, or 7-membered non-aromatic monocyclic ring or a 7- or 8-membered non-aromatic bicyclic ring, said ring having exactly 1 ring heteroatom or exactly 2 ring heteroatoms, wherein each of said ring heteroatoms is independently N, O, or S; and is optionally substituted.
In one embodiment, each —$R^{A3}$ or each —$R^{B3}$, if present, is independently pyrrolidinyl, piperidinyl, piperazinyl, morpholinyl, tetrahydrofuranyl, or tetrahydropyranyl.
—$R^{A4}$ and —$R^{B4}$
In one embodiment, each —$R^{A4}$ or each —$R^{B4}$, where present, is independently $C_{6-10}$carboaryl.

In one embodiment, each —$R^{A4}$ or each —$R^{B4}$, where present, is independently phenyl.

—$R^{A5}$ and —$R^{B5}$

In one embodiment, each —$R^{A5}$ or each —$R^{B5}$, if present, is independently $C_{5-8}$heteroaryl.

In one embodiment, each —$R^{A5}$ or each —$R^{B5}$, if present, is independently furanyl, thienyl, pyrrolyl, imidazolyl, pyrazolyl, triazolyl, oxazolyl, isoxazolyl, thiazolyl, isothiazolyl, pyridyl, pyrimidinyl, or pyridazinyl, and is optionally substituted.

In one embodiment, each —$R^{A5}$ or each —$R^{B5}$, if present is independently pyridyl.

-$L^A$- and -$L^B$-

In one embodiment, each -$L^A$- or each -$L^B$-, where present, is independently saturated $C_{1-3}$alkylene.

In one embodiment, each -$L^A$- or each -$L^B$-, where present, is independently —$CH_2$—.

In one embodiment, each -$L^A$- or each -$L^B$-, where present, is independently —$CH_2CH_2$—.

—$R^{A1}$, $R^{A2}$, —$R^{A3}$, —$R^{A4}$, —$R^{A5}$, and -$L^A$

In one embodiment, each —$R^{A1}$, —$R^{A2}$, —$R^{A3}$, —$R^{A4}$, —$R^{A5}$, and -$L^A$-, where present, is optionally substituted, for example, with one or more substituents.

In one embodiment, each —$R^{A1}$, —$R^{A2}$, —$R^{A3}$, —$R^{A4}$, —$R^{A5}$ and -$L^A$-, where present, is unsubstituted.

In one embodiment, each —$R^{A1}$, —$R^{A2}$, —$R^{A3}$, —$R^{A4}$, —$R^{A5}$, and -$L^A$-, where present, is optionally substituted, for example, with one or more substituents —$R^{AA}$.

—$R^{AA}$

In one embodiment, each —$R^{AA}$, where present, is independently:
- —F, —Cl, —Br, —I,
- —$R^{C1}$,
- —$CF_3$, —$OCF_3$,
- —OH, -$L^C$-OH,
- —$OR^{C1}$, -$L^C$-$OR^{C1}$,
- —SH, —$SR^{C1}$,
- —CN,
- —$NO_2$,
- —$NH_2$, —$NHR^{C1}$, —$NR^{C1}{}_2$, —$NR^{C2}R^{C3}$,
- -$L^C$-$NH_2$, -$L^C$-$NHR^{C1}$, -$L^C$-$NR^{C1}{}_2$, -$L^C$-$NR^{C2}R^{C3}$,
- —C(=O)OH, —C(=O)$OR^{C1}$,
- —C(=O)$NH_2$, —C(=O)$NHR^{C1}$, —C(=O)$NR^{C1}{}_2$, or —C(=O)$NR^{C2}R^{C3}$;

wherein:
- each —$R^{C1}$ is independently saturated aliphatic $C_{1-4}$alkyl, phenyl, or benzyl;
- each -$L^C$- is independently saturated aliphatic $C_{1-5}$alkylene; and
- in each group —$NR^{C2}R^{C3}$, —$R^{C2}$ and —$R^{C3}$, taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, each —$R^{AA}$, where present, is independently:
- —F, —Cl, —Br, —I,
- —$R^{C1}$,
- —$CF_3$,
- —OH,
- —SH, —$SR^{C1}$,
- —CN,
- —$NO_2$,
- —$NH_2$, —$NR^{C1}{}_2$, —$NR^{C2}R^{C3}$,
- -$L^C$-$NH_2$, -$L^C$-$NHR^{C1}$, -$L^C$-$NR^{C1}{}_2$, -$L^C$-$NR^{C2}R^{C3}$,
- —C(=O)OH, —C(=O)$OR^{C1}$,
- —C(=O)$NH_2$, —C(=O)$NHR^{C1}$, —C(=O)$NR^{C1}{}_2$, or —C(=O)$NR^{C2}R^{C3}$.

In one embodiment, each —$R^{AA}$, where present, is independently:
- —F, —Cl, —Br, —I,
- —$R^{C1}$,
- —$CF_3$,
- —$OR^{C1}$,
- —CN,
- —$NO_2$,
- —$NH_2$, —$NHR^{C1}$, —$NR^{C1}{}_2$, —$NR^{C2}R^{C3}$,
- -$L^C$-$NH_2$, -$L^C$-$NHR^{C1}$, -$L^C$-$NR^{C1}{}_2$, -$L^C$-$NR^{C2}R^{C3}$,
- —C(=O)OH, —C(=O)$OR^{C1}$,
- —C(=O)$NH_2$, —C(=O)$NHR^{C1}$, —C(=O)$NR^{C1}{}_2$, or —C(=O)$NR^{C2}R^{C3}$.

In one embodiment, each —$R^{AA}$, where present, is independently:
- —F, —Cl, —Br, —I,
- —$R^{C1}$,
- —$CF_3$,
- —$OR^{C1}$,
- —$NR^{C1}{}_2$, —$NR^{C2}R^{C3}$,
- -$L^C$-$NR^{C1}{}_2$, -$L^C$-$NR^{C2}R^{C3}$,
- —C(=O)OH, —C(=O)$OR^{C1}$,
- —C(=O)$NH_2$, —C(=O)$NHR^{C1}$, —C(=O)$NR^{C1}{}_2$, or —C(=O)$NR^{C2}R^{C3}$.

In one embodiment, each —$R^{AA}$, where present, is independently:
- —F, —Cl, —Br, —I,
- —$R^{C1}$,
- —$CF_3$,
- —$OR^{C1}$.

—$R^{C1}$

In one embodiment, each —$R^{C1}$, where present, is independently saturated aliphatic $C_{1-4}$alkyl, phenyl, or benzyl.

In one embodiment, each —$R^{C1}$, where present, is independently saturated aliphatic $C_{1-4}$alkyl.

In one embodiment, each —$R^{C1}$, where present, is independently phenyl.

In one embodiment, each —$R^{C1}$, where present, is independently benzyl.

-$L^C$-

In one embodiment, each -$L^C$-, where present, is independently saturated aliphatic $C_{1-5}$alkylene.

In one embodiment, each -$L^C$-, where present, is independently —$CH_2$—.

In one embodiment, each -$L^C$-, where present, is independently —$CH_2CH_2$—.

—$R^{C2}$ and —$R^{C3}$

In one embodiment, —$R^{C2}$ and —$R^{C3}$ taken together with the nitrogen atom to which they are attached, form a 4-, 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N or O.

In one embodiment, —$R^{C2}$ and —$R^{C3}$ taken together with the nitrogen atom to which they are attached, form a pyrrolidine, piperazine, piperidine, morpholine, or thiomorpholine ring.

In one embodiment, —$R^{C2}$ and —$R^{C3}$ taken together with the nitrogen atom to which they are attached, form a morpholine or thiomorpholine ring.

In one embodiment, —$R^{C2}$ and —$R^{C3}$ taken together with the nitrogen atom to which they are attached, form a morpholine ring.

Y

In one embodiment, Y is independently S or O.

In one embodiment, Y is independently S.

In one embodiment, Y is independently O.

In one embodiment, Y is S where one of —$R^{N1}$ and —$R^{N2}$ is other than —H.

In one embodiment, Y is O where —$R^{N1}$ and —$R^{N2}$ are each —H.

—$R^{N1}$ and —$R^{N2}$

In one embodiment, —$R^{N1}$ and —$R^2$ are each independently selected from —H or saturated $C_{1-6}$alkyl.

In one embodiment, —$R^{N1}$ is independently —H.

In one embodiment, —$R^{N1}$ is independently saturated $C_{1-6}$alkyl.

In one embodiment, —$R^{N1}$ is independently saturated aliphatic $C_{1-6}$alkyl.

In one embodiment, —$R^{N1}$ is independently -Et.

In one embodiment, —$R^{N2}$ is independently —H.

In one embodiment, —$R^{N2}$ is independently saturated $C_{1-5}$alkyl.

In one embodiment, —$R^{N2}$ is independently saturated aliphatic $C_{1-6}$alkyl.

In one embodiment, —$R^{N2}$ is independently -Et.

In one embodiment, —$R^{N1}$ and —$R^{N2}$ are the same.

In one embodiment, —$R^{N1}$ and —$R^{N2}$ are different.

In one embodiment, —$R^{N1}$ and —$R^{N2}$ are each —H.

In one embodiment, —$R^{N1}$ and —$R^{N2}$ are each -Et.

In one embodiment, —$R^{N1}$ and —$R^{N2}$ taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S.

In one embodiment, —$R^{N1}$ and —$R^{N2}$ taken together with the nitrogen atom to which they are attached, form a 6-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S.

In one embodiment, —$R^{N1}$ and —$R^{N2}$ taken together with the nitrogen atom to which they are attached, form a pyrrolidine, piperazine, piperidine, morpholine, or thiomorpholine ring.

In one embodiment, —$R^{N1}$ and —$R^{N2}$ taken together with the nitrogen atom to which they are attached, form a morpholine or thiomorpholine ring.

In one embodiment, —$R^{N1}$ and —$R^{N2}$ taken together with the nitrogen atom to which they are attached, form a morpholine ring.

4a and 9a Bond

In one embodiment, the dashed line indicates that the bond is a single bond or a double bond between the 4a and 9a atoms.

In one embodiment, the dashed line indicates that the bond is a single bond between the 4a and 9a atoms.

In one embodiment, the dashed line indicates that the bond is a double bond between the 4a and 9a atoms.

Combinations

Each and every compatible combination of the embodiments described above, and below, is explicitly disclosed herein, as if each and every combination was individually and explicitly recited.

Substantially Purified Forms

One aspect of the present invention pertains to compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Salts

It may be convenient or desirable to prepare, purify, and/or handle a corresponding salt of the compound. For example, if the compound is anionic, or has a functional group which may be anionic (e.g., —COOH may be —COO⁻), then a salt may be formed with a suitable cation. Examples of suitable inorganic cations include, but are not limited to, alkali metal ions such as Na⁺ and K⁺, alkaline earth cations such as Ca²⁺ and Mg²⁺, and other cations such as Al⁺³. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Formulations

The compounds of formula (I) may be provided in a composition or formulation for administration to a subject, for example a subject having AD. While it is possible for the compound to be used (e.g., administered) alone, it is often preferable to present it as a composition or formulation.

In one aspect of the invention there is provided a method of preparing a composition or formulation comprising a compound of formula (I). The method includes the synthesis of a compound of formula (I) comprising one or more of the steps described herein. In one embodiment, the method further comprises the step of admixing at least one compound of formula (I), as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

In one embodiment, the composition is a pharmaceutical composition (e.g., formulation, preparation, medicament) comprising a compound of formula (I), as described herein, and a pharmaceutically acceptable carrier, diluent, or excipient.

In one embodiment, the composition is a pharmaceutical composition comprising at least one compound of formula (I), as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, Handbook of Pharmaceutical Additives, 2nd Edition (eds. M. Ash and I. Ash), 2001 (Synapse Information Resources, Inc., Endicott, New York, USA); Remington: The Science and Practice of Pharmacy, 20th Edition (ed. Gennaro et al.), 2000, Lippincott, Williams & Wilkins, Baltimore; and Handbook of Pharmaceutical Excipients, 2nd Edition (eds A. Wade and P. J. Weller), 1994, American Pharmaceutical Association, Washington and The Pharmaceutical Press, London.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Use of Compounds and Compositions in Therapy

In one aspect the present invention provides compounds of formula (I) and formulations comprising compounds of formula (I) as described herein for use in therapy.

In other aspects, the invention pertains to compounds obtained or obtainable by the methods described herein for use in therapy.

Doody at el. have noted that Dimebon weakly inhibits butyrylcholinesterase and acetyl cholinesterase, weakly blocks the N-methyl-D-aspartate receptor signalling pathway, and inhibits mitochondrial permeability transition pore opening.

Yamashita et al. have noted that Dimebon inhibits aggregation of TDP-43 in cellular models of amyotrophic lateral sclerosis (ALS) and frontotemporal lobar degeneration with ubiquinated inclusions (FLTD-U).

Dimebon has also shown neuroprotective effects in models for Alzheimer's disease and Huntington's disease.

The compounds and compositions described herein may reverse or inhibit the aggregation of tau protein (e.g. in the form of paired helical filaments (PHFs), optionally in neurofibrillary tangles (NFTs)) in the brain of a mammal.

As discussed below, various tauopathy disorders that have been recognized which feature prominent tau pathology in neurons and/or glia and this term has been used in the art for several years. The similarities between these pathological inclusions and the characteristic tau inclusions in diseases such as AD indicate that the structural features are shared and that it is the topographic distribution of the pathology that is responsible for the different clinical phenotypes observed. In addition to specific diseases discussed below, those skilled in the art can identify tauopathies by combinations of cognitive or behavioural symptoms, plus additionally through the use of appropriate ligands for aggregated tau as visualised using PET or MRI, such as those described in WO02/075318.

One aspect of the present invention pertains to a method of treatment or prophylaxis of a tauopathy condition in a patient, comprising administering to said patient a therapeutically-effective amount of a compound of formula (I), as described herein.

Aspects of the present invention relate to "tauopathies". As well as Alzheimer's disease (AD), the pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); FTD with parkinsonism linked to chromosome 17 (FTDP-17); disinhibition-dementia-parkinsonism-amyotrophy complex (DDPAC); pallido-ponto-nigral degeneration (PPND); Guam-amyotrophic lateral sclerosit (ALS) syndrome; pallido-nigro-luysian degeneration (PNLD); cortico-basal degeneration (CBD); Dementia with Argyrophilic grains (AgD); Dementia pugilistica (DP) wherein despite different topography, NFTs are similar to those observed in AD (H of P. R., Bouras C., Buee L., Delacourte A., Peri D. P. and Morrison J. H. (1992) Differential distribution of neurofibrillary tangles in the cerebral cortex of dementia pugilistica and Alzheimer's disease cases. Acta Neuropathol. 85, 23-30). Chronic traumatic encephalopathy (CTE), a tauopathy including DP as well as repeated and sports-related concussion (McKee, A., Cantu, R., Nowinski, C., Hedley-Whyte, E., Gavett, B., Budson, A., Santini, V., Lee, H.-S., Kubilus, C. & Stern, R. (2009) Chronic traumatic encephalopathy in athletes: progressive tauopathy after repetitive head injury. Journal of Neuropathology & Experimental Neurology 68, 709-735). Others are discussed in Wischik et al. 2000, loc. cit, for detailed discussion—especially Table 5.1).

Abnormal tau in NFTs is found also in Down's Syndrome (DS) (Flament S., Delacourte A. and Mann D. M. A. (1990) Phosphorylation of tau proteins: a major event during the process of neurofibrillary degeneration. A comparative study between AD and Down's syndrome. Brain Res., 516, 15-19). Also Dementia with Lewy bodies (DLB) (Harrington, C. R., Perry, R. H., Perry, E. K., Hurt, J., McKeith, I. G., Roth, M. & Wischik, C. M. (1994) Senile dementia of Lewy body type and Alzheimer type are biochemically distinct in terms of paired helical filaments and hyperphosphorylated tau protein. Dementia 5, 215-228). Tau-positive NFTs are also found in Postencephalitic parkinsonism (PEP) (Hof P. R., Charpiot, A., Delacourte A., Buee, L., Purohit, D., Perl D. P. and Bouras, C. (1992) Distribution of neurofibrillary tangles and senile plaques in the cerebral cortex in postencephalitic parkinsonism. Neurosci. Lett. 139, 10-14). Glial tau tangles are observed in Subacute sclerosing panencephalitis (SSPE) (Ikeda K., Akiyama H., Kondo H., Arai T., Arai N. and Yagishita S. (1995) Numerous glial fibrillary tangles in oligodendroglia in cases of subacute sclerosing panencephalitis with neurofibrillary tangles. Neurosci. Lett., 194, 133-135).

Additionally there is a growing consensus in the literature that a tau pathology may also contribute more generally to cognitive deficits and decline, including in mild cognitive impairment (MCI) (see e.g. Braak, H., Del Tredici, K, Braak, E. (2003) Spectrum of pathology. In Mild cognitive impairment: Aging to Alzheimer's disease edited by Petersen, R. C.; pp. 149-189).

In this and all other aspects of the invention relating to tauopathies, preferably the tauopathy is selected from the list consisting of the indications above, i.e., AD, Pick's disease, PSP, FTD, FTDP-17, DDPAC, PPND, Guam-ALS syndrome, PNLD, and CBD and AgD, DS, SSPE, DP, PEP, DLB, CTE and MC1.

In one preferred embodiment the tauopathy is Alzheimer's disease (AD).

One aspect of the present invention pertains to a compound of formula (I), as described herein, for use in a method of treatment or prophylaxis (e.g., of a tauopathy condition) of the human or animal body by therapy.

One aspect of the present invention pertains to use of a compound of formula (I), as described herein, in the manufacture of a medicament for use in the treatment or prophylaxis of a tauopathy condition.

A further embodiment is a method of treatment or prophylaxis of a disease of tau protein aggregation as described herein, which method comprises administering to a subject a compound of formula (I), or therapeutic composition comprising the same, such as to inhibit the aggregation of the tau protein associated with said disease state.

EXAMPLES

The following syntheses are provided solely for illustrative purposes and are not intended to limit the scope of the invention, as described herein.

Synthesis 1a

6-Methyl-3-pyridylthioacetmorpholide

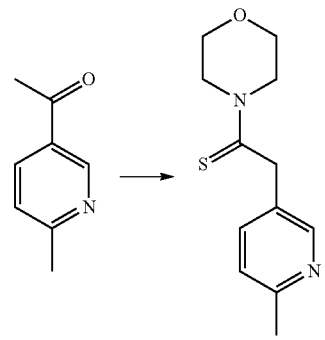

5-Acetyl-2-methylpyridine (36.75 mmol, 5.00 g), morpholine (1.7 eq., 62.475 mmol, 5.44 g, 5.46 cm$^3$), and sulphur (1.6 eq., 58.8 mmol, 1.88 g) were combined in a flask and heated at reflux for 17 hours. The reaction was then cooled to room temperature, and poured into water (100 cm$^3$). The resulting opaque solution was extracted with CHCl$_3$ (3×100 cm$^3$). The combined extracts were dried (MgSO$_4$), and the solvent removed to yield a dark oil. Light petrol (50 cm$^3$) was added to this oil, stirred vigorously, and the resulting mixture evaporated to yield a crude yellow solid, which was filtered, and washed with additional petrol (50 cm$^3$) to give the product (9.338 g, 93.3%).

$\delta_H$ (250 MHz, CDCl$_3$) 8.31 (1H, s, Ar), 7.58 (1H, d, J 7.7, Ar), 7.06 (1H, d, J 7.7, Ar), 4.26 (2H, t, J 4.3, CH$_2$), 4.20 (2H, s, CH$_2$), 3.60 (2H, t, J 4.3, CH$_2$), 2.47 (3H, s, CH$_3$); $\delta_C$ (62.5 MHz, CDCl$_3$) 199.1 (C=S), 157.4 (Ar), 148.5 (Ar), 135.8 (Ar), 128.4 (Ar), 123.4 (Ar), 66.3 (CH$_2$), 50.6 (CH$_2$), 50.1 (CH$_2$), 24.0 (CH$_3$).

The synthesis of this compound has been described previously by Sperber et al.

Synthesis 1b i) 5-Acetyl-2-methylpyridine (method of Masamichi Maruoka et al.)

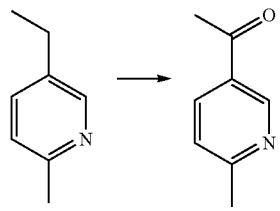

The reactor was charged with 5-ethyl-2-methylpyridine (200 cm$^3$, 1.5 mol) and cooled to 5° C. Concentrated H$_2$SO$_4$ (132 cm$^3$, 1.3 mol) was added cautiously, and the medium stirred for 15 minutes until homogeneous and adequately cool. AcOH (236 cm³, 4.1 mol) was added, followed by Ac$_2$O (173 cm³, 2.4 mol) and the medium stirred for 15 minutes. Solid CrO$_3$ (212 g, 2.12 mol) was added cautiously over ~3 hours taking great care to keep the internal temperature between 10-20° C. The reaction was then allowed to stir at 20° C. for an additional 3 hours. The crude reaction medium was poured onto ice (1 kg), and this aqueous medium returned to the reactor vessel, and cautiously made basic with solid Na$_2$CO$_3$. CHCl$_3$ (1 L) was added, and the reactor stirred vigorously for 10 mins. The organic phase was collected. This extraction process was repeated a further 2 times. The combined organics are dried (MgSO$_4$) and solvent removed.

The resulting brown oil was a mixture of starting material and product (typically 2:1). Starting material can be recovered by vacuum distillation (bp. 35-42° C. @ 10 mmHg) to leave a brown residue (63.6 g, 31%) which gives a ¹H NMR spectrum consistent with 5-acetyl-2-methylpyridine.

δ$_H$ (250 MHz, CDCl$_3$) 8.82 (1H, s, Ar), 7.91 (1H, d, J 7.7, Ar), 7.06 (1H, d, J 7.7, Ar), 2.40 (6H, s, CH$_3$);

ii) 6-Methyl-3-pyridylthioacetmorpholide hydrochloride

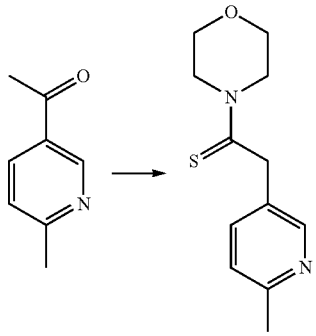

5-Acetyl-2-methylpyridine (63 g, 471 mmol), morpholine (70 cm³, 800 mmol), and sulphur (24 g, 753 mmol) were combined in a flask and heated to reflux for 16 hours.

The reaction was then cooled to room temperature, and poured into H$_2$O (1 L). This opaque solution was extracted with CHCl$_3$ (3×1 L). The combined extracts were dried (MgSO$_4$), and solvent removed to yield a dark oil. This was diluted to 500 cm³ with THF, and concentrated HCl added (30 cm³). The precipitated product was isolated by filtration to yield the hydrochloride salt as a light brown solid (113 g, 87.9%).

δ$_H$ (250 MHz, CDCl$_3$) 8.58 (1H, s, Ar), 8.37 (1H, d, J 8.0, Ar), 7.85 (1H, d, J 8.0, Ar), 4.35 (2H, s, CH$_2$), 4.20 (2H, mult, CH$_2$), 3.90 (2H, mult, CH$_2$), 3.77 (4H, m, CH$_2$), 2.74 (3H, s, CH$_3$).

Synthesis 2

N,N-Diethyl-2-(6-methyl-pyridin-3-yl)-thioacetamide

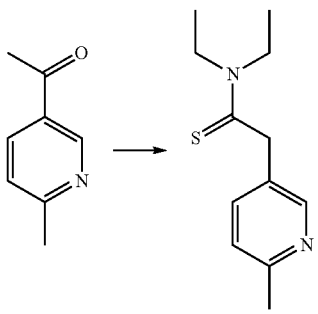

The procedure was the same as that used in example 1 above. Thus, 5-acetyl-2-methylpyridine (7.4 mmol, 1.00 g), diethylamine (1.7 eq., 12.5 mmol, 0.919 g, 1.3 cm³), and sulphur (1.6 eq., 11.84 mmol, 0.379 g) were refluxed and worked up as previously described. Treatment of the crude residue with petrol did not induce crystallisation, so the title compound was isolated by flash chromatography, first eluting impurities with 1:1 petrol/EtOAc, then eluting the product with EtOAc (R$_f$=0.392 in EtOAc). The product was obtained as a yellow oil (0.606 g, 36.8%).

δ$_H$ (250 MHz, CDCl$_3$) 8.14 (1H, s, Ar), 7.38 (1H, d, J 7.9, Ar), 6.90 (1H, d, J 7.9, Ar), 3.96 (2H, s, CH$_2$), 3.74 (2H, q, J 7.0 CH$_2$), 3.28 (2H, q, J 7.0, CH$_2$), 2.28 (3H, s, CH$_3$), 1.02 (3H, t, J 7.0, CH$_3$), 0.94 (3H, t, J 7.0, CH$_3$); δc (62.5 MHz, CDCl$_3$) 197.8 (C=S), 156.7 (Ar), 148.5 (Ar), 135.9 (Ar), 129.1 (Ar), 123.1 (Ar), 47.6 (CH$_2$), 46.5 (CH$_2$), 46.4 (CH$_2$), 23.8 (CH$_3$), 13.4 (CH$_3$), 11.0 (CH$_3$).

Synthesis 3

2-(6-Methyl-pyridin-3-yl)-acetamide

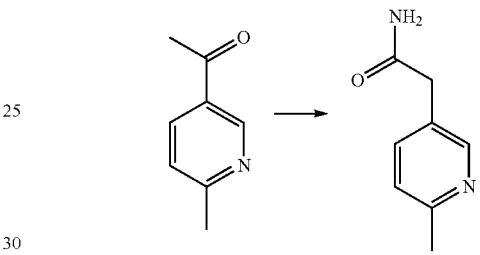

To a Schlenk tube charged with 5-acetyl-2-methylpyridine (937 mg, 6.9 mmol, 1.0 eq), was added ammonia solution (35% wt/vol, 1.20 cm³, 25 mmol, 3.6 eq) and pyridine (1 cm³). The vessel was sealed and the homogeneous solution shaken vigorously, and allowed to stand for 30 minutes. Sulfur (1.25 g, 38.9 mmol, 5.6 eq) was then added, and the vessel sealed, and heated to 160° C. for 17 hours. The cooled reaction medium was rinsed into a round bottom flask using the minimum quantity of distilled water (~5 cm³), and solvent removed in vacuo to leave a solid yellow residue, which was purified by column chromatography, eluting with 4:1 EtOAc/MeOH and collecting the fraction with R$_f$=0.282, to yield the desired product as fine colourless needles (151 mg, 15%).

mp 175-177° C. (lit 168-169° C.); δ$_H$ (250 MHz; CD$_3$OD) 8.27 (1H, s, Ar), 7.59 (1H, d, J 8.1, Ar), 7.19 (1H, d, J 8.1, Ar), 4.75 (2H, s, NH$_2$), 3.46 (2H, s, CH$_2$), 2.47 (3H, s, CH$_3$).

The title product may be hydrolysed to the corresponding carboxylic acid by hydrolysis as exemplified below for the thioamide compounds.

Synthesis 4a

6-Methyl-3-pyridineacetic acid

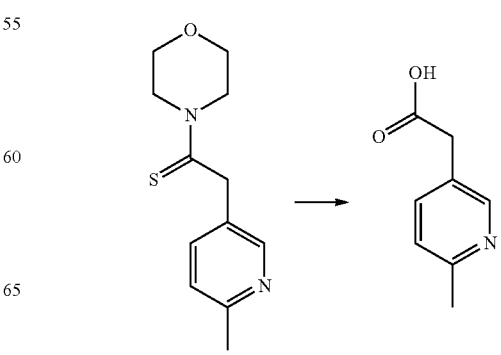

Crude 2-(6-methyl-pyridin-3-yl)-1-morpholin-4-yl-ethanethione (39.5 mmol, 9.685 g) was suspended in 2:1 H₂O/EtOH (40 mL). NaOH (3.3 eq., 118.5 mmol, 4.8 g) was added and the reaction heated to reflux for 16 hours. The volatiles were then removed from the cooled reaction medium, and the pH adjusted to precisely pH 7.0 with 3.0 M HCl. The solvent was removed and the residue slurried in boiling methanol, filtered whilst hot, and the filtrate evaporated to dryness. This crude product contains residual free morpholine, which was removed by flash column chromatography, eluting with 9:1 EtOAc/MeOH. The fractions were analysed by TLC eluting with 1:1 EtOAc/MeOH ($R_f$=0.209). The product was obtained in 46% yield.

$\delta_H$ (250 MHz, CD₃OD) 8.33 (1H, s, Ar), 7.69 (1H, d, J 7.9, Ar), 7.28 (1H, d, J 7.9, Ar), 3.59 (2H, s, CH₂), 2.51 (3H, s, CH₃); $\delta_C$ (62.5 MHz, CD₃OD) 176.6 (C=O), 157.1 (Ar), 150.0 (Ar), 140.3 (Ar), 131.4 (Ar), 125.0 (Ar), 40.3 (CH₂), 23.3 (CH₃).

Synthesis 4b

6-Methyl-3-pyridineacetic acid (modified method)

Crude 2-(6-Methyl-pyridin-3-yl)-1-morpholin-4-yl-ethanethione (39.5 mmol, 9.685 g) was suspended in 2:1 H₂O/EtOH (75 cm³). NaOH (3.3 eq., 118.5 mmol, 4.8 g) added and the reaction heated to reflux for 16 hours. Volatiles were then removed from the cooled reaction medium, and the aqueous residue extracted with DCM (3×50 cm³). The pH was adjusted to precisely pH 7.0 with HCl, and a further DCM extraction performed (3×50 cm³). Water was removed from the residue, and the obtained solids slurried in methanol, filtered, and the filtrate evaporated to dryness. The orange solid obtained gave spectroscopic data consistent with the desired product. Mass recovery is typically >100% however this is due to NaCl within the product.

The synthesis of this compound has been described previously by Sperber et al.

This compound has been obtained in crystalline form and a single crystal X-ray structure obtained. Crystallographic data sets were collected on a Bruker Smart APEX2, at 150K, using a full-matrix least-squares refinement on F2.

Synthesis 5

6-Methyl-3-pyridineacetic acid

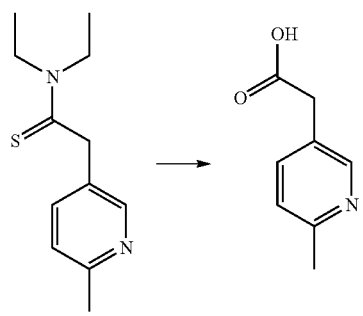

Crude N,N-diethyl-2-(6-methyl-pyridin-3-yl)-thioacetamide was hydrolysed with NaOH as described above in Synthesis 4a. The product acid was obtained in 28% yield after purification.

The analytical data were identical to those reported above in Synthesis 4.

Synthesis 6

2-(6-Methyl-pyridin-3-yl)-N-p-tolyl-acetamide

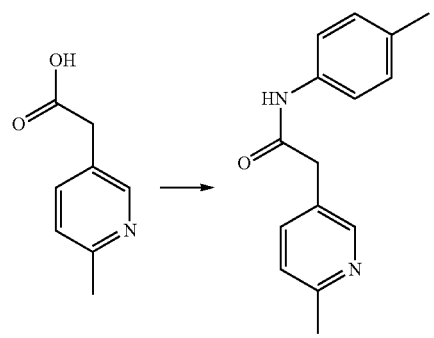 [SMILES: Cc1ccc(CC(=O)O)cn1 ; Cc1ccc(NC(=O)Cc2ccc(C)nc2)cc1]

Carbodiimide Method (6-Methyl-pyridin-3-yl)-acetic acid (500 mg, 3.3 mmol) was added to DCM (50 cm³). Et₃N (1.0 eq., 0.4 cm³) was then added, followed by p-toluidine (1.5 eq., 4.96 mmol, 531 mg) and DCC (1.1 eq., 3.64 mmol, 750 mg). The cloudy solution was stirred at room temperature under an argon atmosphere for 6 hours, filtered, and the solvent removed. The crude product was purified by flash chromatography, eluting with EtOAc, and collecting the product as the fraction with $R_f$=0.375 (9% yield).

Mixed Anhydride Method (1)

(6-Methyl-pyridin-3-yl)-acetic acid (1.0 g, 6.61 mmol) was placed in a dry flask under an argon atmosphere. Dry THF (100 cm³) was added, followed by N-methylmorpholine (1.0 eq., 6.61 mmol, 0.668 g, 0.73 cm³). The solution was cooled to −78° C. iso-Butyl chloroformate (1.2 eq., 7.932 mmol, 1.08 g, 1.0 cm³) was added, and the solution stirred for 30 min. p-Toluidine (1.0 eq., 6.61 mmol, 0.707 g) was added, and the reaction allowed to warm to room temperature, then stirred for 16 hours. Volatiles were then removed from the reaction, and the residue partitioned between 10% aq. NaHCO₃ solution (100 cm³) and DCM (100 cm³). The organic layer was separated and washed with water (100 cm³), dried (MgSO₄), and solvent removed, to yield a pale yellow solid. This solid was recrystallised from THF (0.494 g, 31%).

The product can be further purified by flash chromatography, eluting with EtOAc, and collecting the product as the fraction with $R_f$=0.375.

Mixed Anhydride Method (2)

(6-Methyl-pyridin-3-yl)-acetic acid (1.0 g, 6.6 mmol) was placed in a flask under an argon atmosphere, and dry DMF (100 cm³) added, followed by Bu₄NBF₄ (218 mg, 0.66 mmol). The solution was stirred for 5 minutes to favour homogeneity, and then cooled to an internal temperature of ~−40° C. N-methylmorpholine (0.75 cm³, 6.6 mmol) was added, followed by isobutyl chloroformate (0.83 cm³, 13.6 mmol). The solution was stirred at this temperature 30 minutes, p-toluidine (710 mg, 6.6 mmol) added, and the coolant removed. The solution was stirred at room temperature under argon for a further 16 hours. Volatiles were then removed by vacuum distillation, and the residue dissolved in $CHCl_3$ (50 $cm^3$), washed sequentially with 10% $NaHCO_3$ solution (50 $cm^3$), $H_2O$ (50 $cm^3$), and dried ($MgSO_4$). Removal of solvent furnished a crude yellow solid which was purified by flash column chromatography on $SiO_2$ (10×5 cm) eluting with EtOAc. The desired product was obtained as colourless prisms (1.13 g, 71.0%).

$\delta_H$ (250 MHz, $CDCl_3$) 8.35 (1H, s, NH), 8.30 (1H, s, Ar), 7.59 (1H, d, J 8.2, Ar), 7.32 (2H, d, J 7.9, Ph), 7.10 (1H, d, J 8.2, Ar), 7.02 (2H, d, J 7.9, Ph), 3.57 (2H, s, $CH_2$), 2.51 (3H, s, $CH_3$), 2.26 (3H, s, $CH_3$); $\delta_C$ (62.5 MHz, $CDCl_3$) 168.6 (C=O), 157.4 (Ar), 149.4 (Ar), 137.4 (Ph), 135.3 (Ar), 134.2 (Ar), 129.4 (Ph), 127.8 (Ar), 123.5 (Ph), 120.2 (Ph), 40.9 ($CH_2$), 24.0 ($CH_3$), 20.9 ($CH_3$). MS ($Cl^+$): calc. 241.1341. found 241.1340 $[M+H]^+$; mp 146-150° C.

This compound has been obtained in crystalline form and a single crystal X-ray structure obtained. Crystallographic data sets were collected on a Bruker Smart APEX2, at 150K, using a full-matrix least-squares refinement on F2.

Synthesis 7a

[2-(6-Methyl-pyridin-3-yl)-ethyl]-p-tolyl-amine

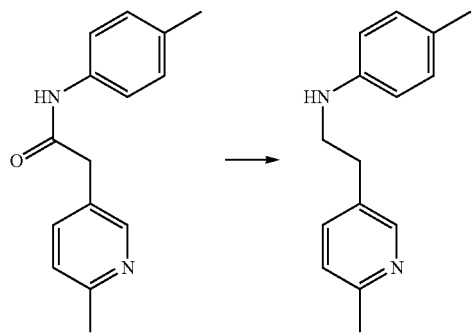 [SMILES: Cc1ccc(NC(=O)Cc2ccc(C)nc2)cc1 ; Cc1ccc(NCCc2ccc(C)nc2)cc1]

2-(6-Methyl-pyridin-3-yl)-N-p-tolyl-acetamide (0.960 g, 4 mmol) was dissolved in dry THF (20 $cm^3$), and cooled to 0° C. $LiAlH_4$ (5.0 eq., 20 mmol, 10 ml of a 2.0 M solution in THF) was added dropwise at first, until no more gas evolution was observed (~0.5 ml), and then the remaining $LiAlH_4$ solution was added in one portion. The resulting solution was heated to reflux for 16 hours with stirring. Wet diethyl ether was then added until no further gas evolution was observed, the resulting medium filtered, and the residue washed with ether (~50 $cm^3$). The filtrate was dried ($MgSO_4$), and the solvent removed to yield a crude yellow oil. The oil was purified by flash chromatography, eluting with 1:1 petrol (40-60)/EtOAc. The product was collected as the fraction with $R_f$=0.294. The product was obtained as a pale yellow oil (254 mg, 28%).

The conditions for the reaction were modified in order to improve the yield of the amine product. The modified conditions used and the results of reactions using those conditions are set out in Table 1 below.

TABLE 1

| Reaction | Amide (mmol) | THF ($cm^3$) | Concentration (M) | Reaction time (h) | Conversion (%) | Yield (%) |
|---|---|---|---|---|---|---|
| Unmodified | 4.0 | 20 | 0.2 | 16 | 68 | 28.0 |
| 1 | 0.3 | 3 | 0.1 | 20 | NA | 23.0 |
| 2 | 2.3 | 20 | 0.1 | 40 | NA | 21.3 |
| 3 | 2.0 | 5 | 0.4 | 16 | 94 | 71.1 |

The molar amount of reducing agent with respect to the amide was held constant. Higher yield of product were obtained at higher concentrations of amide in the reaction medium.

The conversion figure is the percentage of desired product in the crude product mixture to the total amount of starting material and desired product. The percentage was calculated from the $^1$H NMR integral values for a singlet proton in the pyridine ring of the product and starting material.

$\delta_H$ (250 MHz, $CDCl_3$) 8.34 (1H, s, Ar), 7.39 (2H, d, J 7.9, Ar), 7.07 (1H, d, J 7.9, Ar), 6.97 (2H, d, J 7.9, Ph), 6.51 (2H, d, J 7.9, Ph), 3.35 (2H, t, J 6.7, $CH_2$), 2.84 (2H, t, J 6.7, $CH_2$), 2.52 (3H, s, $CH_3$), 2.22 (3H, s, $CH_3$). $\delta_C$ (62.5 MHz, $CDCl_3$) 159.5 (Ar), 149.3 (Ar), 145.4 (Ar), 136.7 (Ph), 131.7 (Ar), 129.9 (Ph), 126.9 (Ar), 123.1 (Ph), 113.2 (Ph), 45.2 ($CH_2$), 32.3 ($CH_2$), 24.0 ($CH_3$), 20.4 ($CH_3$). MS ($Cl^+$): calc. 227.1548. found 227.1548 $[M+H]^+$.

Synthesis 7b

[2-(6-Methyl-pyridin-3-yl)-ethyl]-p-tolyl-amine (modified method)

2-(6-Methyl-pyridin-3-yl)-N-p-tolyl-acetamide (0.25 g, 1 mmol) was dissolved in DCM (5 $cm^3$) under an argon atmosphere. $Bu_4NBH_4$ (0.8 g, 3 mmol) was added in one portion. The resulting solution was heated to reflux for 16 hours with stirring. Volatiles were then removed in vacuo and the residue suspended in 1.0 M HCl (5 $cm^3$) and heated to reflux for 20 minutes. $Na_2CO_3$ was then added to the cooled solution until no further gas evolution was observed. The solution was extracted with $Et_2O$ (3×5 $cm^3$), the extracts combined, washed with $H_2O$ (20 $cm^3$), dried ($MgSO_4$), and solvent removed to yield a tacky yellow oil (217 mg, 96%). NMR spectroscopy of this oil, showed the desired product was present in good purity.

$\delta_H$ (250 MHz, $CDCl_3$) 8.34 (1H, s, Ar), 7.39 (2H, d, J 7.9, Ar), 7.07 (1H, d, J 7.9, Ar), 6.97 (2H, d, J 7.9, Ph), 6.51 (2H, d, J 7.9, Ph), 3.35 (2H, t, J 6.7, $CH_2$), 2.84 (2H, t, J 6.7, $CH_2$), 2.52 (3H, s, $CH_3$), 2.22 (3H, s, $CH_3$); $\delta_C$ (62.5 MHz, $CDCl_3$) 159.5 (Ar), 149.3 (Ar), 145.4 (Ar), 136.7 (Ph), 131.7 (Ar), 129.9 (Ph), 126.9 (Ar), 123.1 (Ph), 113.2 (Ph), 45.2 ($CH_2$), 32.3 ($CH_2$), 24.0 ($CH_3$), 20.4 ($CH_3$);

The inventors have used compound 1, as synthesised by the methods described herein, to prepare dimebon.

Synthesis 8

2-Methyl-5-(N-nitroso-2-p-tolylaminoethyl)pyridine

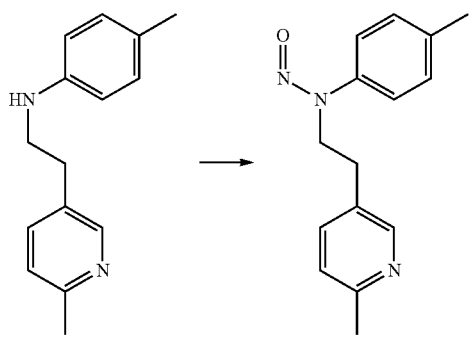 [SMILES: Cc1ccc(NCCc2ccc(C)nc2)cc1 ; Cc1ccc(N(CCc2ccc(C)nc2)N=O)cc1]

[2-(6-Methyl-pyridin-3-yl)-ethyl]-p-tolyl-amine (693.4 mg, 3 mmol) was dissolved in EtOH (8 cm³) and HCl added (3 cm³ of a 1.0 M solution, 3 mmol). The resulting solution was cooled to 5° C. NaONO (232.5 mg, 3.37 mmol) was dissolved in H₂O (2 cm³) and cooled to 5° C., before being added slowly to the starting material solution, such that the internal temperature remained between 5-10° C. The reaction was allowed to attain room temperature, stoppered, and stirred for an additional 18 hours. The stopper was then removed and a gentle air stream blown across the medium to remove EtOH. The resulting crystalline precipitate was removed by filtration, washed with H₂O (10 cm³) and placed in a desiccator over SiO₂ until required (612 mg, 78%).

Synthesis 9

N-[2-(6-Methyl-pyridin-3-yl)-ethyl]-N-p-tolyl-hydrazine

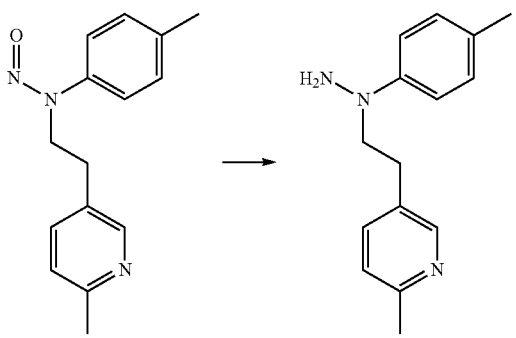 [SMILES: Cc1ccc(N(CCc2ccc(C)nc2)N=O)cc1 ; Cc1ccc(N(N)CCc2ccc(C)nc2)cc1]

Crude 2-methyl-5-(N-nitroso-2-p-tolylaminoethyl)pyridine (612 mg, 2.4 mmol) was dissolved in dry THF (20 cm³) in a dry 3-neck flask under an argon atmosphere and cooled until the internal temperature was between 0-5° C. Solid LiAlH₄ (290 mg, 7.7 mmol) was added and the reaction allowed to warm to room temperature. Following 2 hours stirring at room temperature, the reaction was again cooled to 0° C., and quenched with MeOH until no further gas evolution was observed (~3 cm³). Saturated NaOH solution was then added (3 cm³), followed by H₂O (3 cm³), and the medium extracted with CHCl₃ (3×50 cm³), the combined extracts were dried (MgSO₄), and solvent removed in vacuo to yield a crude orange oil. This could be carried forward to the next step if desired, or stored below 5° C. until required.

Synthesis 10

N'-(1-Methyl-piperidin-4-ylidene)-N-[2-(6-methyl-pyridin-3-yl)-ethyl]-N-p-tolyl-hydrazine

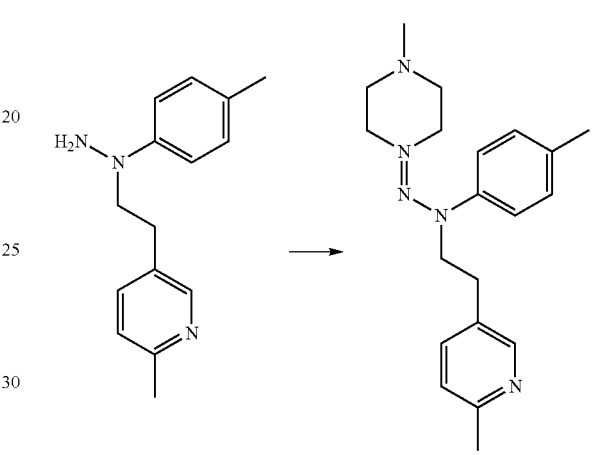

The crude N-[2-(6-methyl-pyridin-3-yl)-ethyl]-N-p-tolyl-hydrazine was dissolved in benzene (20 cm³) and 4 Å molecular sieves added (~5 g), followed by 1-methylpiperidin-4-one (346 μL, 3.0 mmol). The reaction was heated to reflux for 2 hours, cooled, and filtered. Solvent was removed in vacuo to yield a crude orange oil.

Synthesis 11

2,8-Dimethyl-5-[2-(6-methyl-pyridin-3-yl)-ethyl]-2,3,4,5-tetrahydro-1H-pyrido[4,3-b]indole (Dimebon)

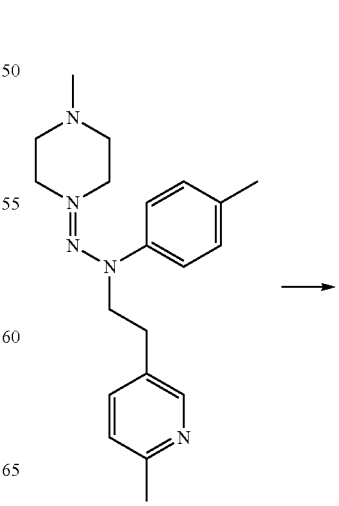

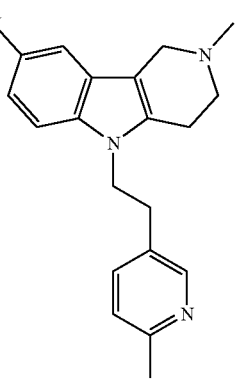

Concentrated HCl (6 cm³) was added to EtOH (4 cm³). The crude N'-(1-methyl-piperidin-4-ylidene)-N-[2-(6-methyl-pyridin-3-yl)-ethyl]-N-p-tolyl-hydrazine was dissolved in this ethanolic HCl and heated to 100° C. for 30 minutes. The reaction was then cooled, and diluted with $H_2O$ (10 cm³), saturated with $Na_2CO_3$, and extracted with $CHCl_3$ (3×50 cm³). The combined extracts were dried ($MgSO_4$) and solvent removed. The residual brown oil was purified by flash column chromatography over $SiO_2$ (10×2 cm) eluting with 1:1 EtOAc/MeOH to provide the desired product as a pale brown powder (612 mg, 63% yield over 3 steps based on last pure starting material (2-methyl-5-(N-nitroso-2-p-tolylaminoethyl)pyridine)).

$\delta_H$ (250 MHz, CDCl$_3$) 8.23 (1H, s, Ar), 7.20 (1H, s, Ar), 7.13 (1H, d, J 7.8, Ar), 7.05 (1H, d, J 7.6, Ar), 6.97 (2H, d, J 8.2, 2×Ar), 4.17 (2H, t, J 7.0, CH2), 3.65 (2H, s, CH2), 2.95 (2H, t, J 7.0, CH2), 2.72 (2H, t, J 5.5, CH2), 2.51 (11H, m); MS (EI⁺): calc. m/z 319.2048. found 319.2042 (M⁺).

Synthesis 12

8-methyl-5-[2-(6-methyl-pyridin-3-yl)-ethyl]-1,3,4, 5-tetrahydro-thiopyrano[4,3-b]indole

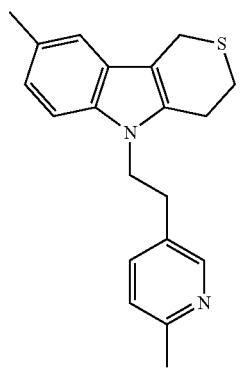 [SMILES: Cc1ccc2c(c1)c1c(n2CCc2ccc(C)nc2)CCSC1]

The method was the same as for Dimebon, using tetrahydro-thiopyran-4-one in place of 1-methylpiperid-4-one. The desired product was isolated as a glassy yellow oil (13.1 mg, 8.7% over three steps based on 2-methyl-5-(N-nitroso-2-p-tolylaminoethyl)pyridine starting material) by column chromatography on SiO2, eluting with 4:1 EtOAc/MeOH.

δH (250 MHz, CDCl3) 8.12 (1H, s, Ar), 7.34 (1H, d (apparent singlet), Ar), 6.81 (4H, m, Ar), 3.99 (2H, t, J 7.6, CH2), 3.88 (2H, s, CH2), 2.89 (2H, d (apparent singlet), CH2), 2.77 (2H, d (apparent singlet), CH2), 2.60 (2H, d (apparent singlet), CH2), 2.48 (3H, s, CH3), 2.39 (3H, s, CH3); MS (ESI⁺): calc. m/z 323.1576. found 323.1585 (M+H⁺).

Synthesis 13

8-methyl-5-[2-(6-methyl-pyridin-3-yl)-ethyl]-1,3,4, 5-tetrahydro-pyrano[4,3-b]indole

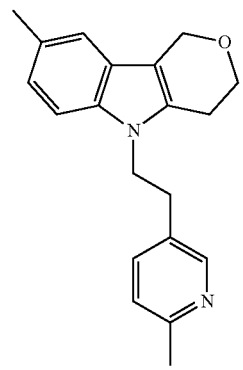 [SMILES: Cc1ccc2c(c1)c1c(n2CCc2ccc(C)nc2)CCOC1]

8-Methyl-5-[2-(6-methyl-pyridin-3-yl)-ethyl]-1,3,4,5-tetrahydro-pyrano[4,3-b]indole is prepared in an analagous manner to Dimebon, except that tetrahydro-pyran-4-one is used in the final step in place of 1-methyl-piperidin-4-one.

REFERENCES

The following references are incorporated by reference herein in their entirety:
U.S. Pat. No. 3,409,628
U.S. Pat. No. 2,611,769
U.S. Pat. No. 2,716,119
WO02/075318
Braak, H., Del Tredici, K, Braak, E. (2003) Spectrum of pathology. In Mild cognitive impairment: Aging to Alzheimer's disease edited by Petersen, R. C.; pp. 149-189
Doody et al., *The Lancet* 2008, 372, 207-215.
Flament et al. *Brain Res.* 1990, 516, 15-19.
Harrington et al. *Dementia* 1994, 5, 215-228.
Hof et al. *Neurosci. Lett.* 1992, 139, 10-14.
Ikeda et al. *Neurosci. Lett.* 1995, 194, 133-135.
Kost et al., *J. Gen. Chem. USSR* 1960, 30, 2538.
Kost et al., *Chemistry of Heterocyclic Compounds,* 1973, 9, 191.
Sperber et al., *J. Am. Chem. Soc.* 1959, 81, 704.
Handbook of Pharmaceutical Additives, 2nd Edition (eds. M. Ash and I. Ash), 2001 (Synapse Information Resources, Inc., Endicott, New York, USA).
Handbook of Pharmaceutical Excipients, 2nd Edition (eds A. Wade and P. J. Weller), 1994, American Pharmaceutical Association, Washington and The Pharmaceutical Press, London.
Medivation Form 10KSB filed 19 Feb. 2008.
Novabiochem Catalog 2006/2007, UK Edition, Merck Biosciences.
Remington: The Science and Practice of Pharmacy, 20th Edition (ed. Gennaro et al.), 2000, Lippincott, Williams & Wilkins, Baltimore.
Wischik et al. (in 'Neurobiology of Alzheimer's Disease', 2nd Edition, 2000, Eds.
Dawbarn, D. and Allen, S. J., *The Molecular and Cellular Neurobiology Series*, Bios Scientific Publishers, Oxford.

Yamashita et al., *FEBS Letters* 2009, 583, 2419-2424.

Medivation press release, 4 Nov. 2009, 'Medivation Reports Third Quarter 2009 Financial Results and Provides Corporate Update', www.medivation.com. Ivachtchenko et al., *Bioorg. Med. Chem. Lett.*, 2009, 19, 3183-3187

R. A. Jones, *Aldrichimica Acta*, 1976, 9(3), 35-45

Masamichi Maruoka, Kakuzo Isgawa, and Yasaburo Fushizaki, "*Nippon Kagaku Zasshi*", 1961, 82, 1279-1284.

The invention claimed is:

1. A method of preparing a compound of formula (II):

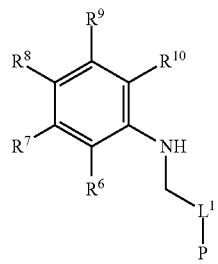

(II)

wherein
—$R^6$, —$R^7$, —$R^8$, and —$R^9$ are each independently —H or —$P^A$;
—$R^{10}$ is independently —H or —$P^A$;
-$L^1$- is independently linear $C_{1-6}$alkylene;
—P is independently pyridine or phenyl, optionally substituted with one or more groups —$P^A$;
each —$P^A$ is independently $C_{1-6}$alkyl;
said method comprising the step of:
reacting a compound of formula (VI):

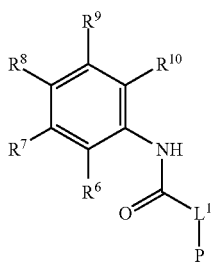

(VI)

with a reducing agent
to form a compound of formula (II).

2. The method according to claim 1, wherein the compound of formula (VI) is reacted with a reducing agent comprising $Bu_4NBH_4$ to form the compound of formula (II).

3. The method according to claim 1, wherein the reaction is performed at reflux in an organic solvent.

4. The reaction according to claim 1, wherein, after reaction, the reaction mixture is hydrolyzed.

5. The method according to claim 1 comprising the steps of, in order:
coupling a compound of formula (V):

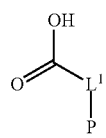

(V)

with a compound of formula (VII):

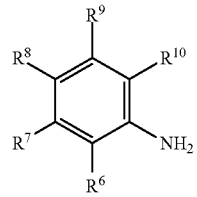

(VII)

to form a compound of formula (VI);
and
reacting the compound of formula (VI) with a reducing agent to form a compound of formula (II).

6. The method according to claim 5, wherein the compound of formula (V) is coupled with the compound of formula (VII) using a coupling reagent which is a carbodiimide.

7. The method according to claim 6, wherein the carbodiimide is DCC, EDC, or DIC.

8. The method according to claim 5, wherein the compound of formula (V) is coupled with the compound of formula (VII) using a coupling reagent which is a haloformate.

9. The method according to claim 8, wherein the haloformate is iso-butyl chloroformate.

10. The method claim 5, wherein a coupling reagent is used in combination with a phase transfer catalyst.

11. The method according to claim 10, wherein the phase transfer catalyst is $Bu_4NBF_4$.

12. The method according to claim 5 wherein a coupling reagent is used in combination with a base.

13. The method according to claim 5 comprising the steps of, in order:
hydrolyzing a compound of formula (IV):

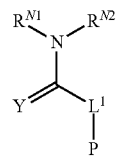

(IV)

wherein
Y is S or O;
—$R^{N1}$ and —$R^{N2}$ are each independently —H or $C_{1-6}$ alkyl, or —$R^{N1}$ and —$R^{N2}$ taken together with the nitrogen atom to which they are attached, form a 5-, 6-, or 7-membered non-aromatic ring having exactly 1 ring heteroatom or exactly 2 ring heteroatoms, wherein one of said exactly 2 ring heteroatoms is N, and the other of said exactly 2 ring heteroatoms is independently N, O, or S;
to form a compound of formula (V);
coupling the compound of formula (V) with a compound of formula (VII) to form a compound of formula (VI); and reacting the compound of formula (VI) with a reducing agent to form a compound of formula (II).

14. The method according to claim 13, wherein the compound of formula (IV) is hydrolyzed by reaction with a base to form the compound of formula (II).

15. The method according to claim 14, wherein the base is sodium hydroxide.

16. The method according to claim 13, wherein, after reaction, an amine by-product, NHR$^{N1}$R$^{N2}$, is separated from the compound of formula (V).

17. The method according to claim 13 comprising the steps of, in order:

reacting a compound of formula (III)

(III)

wherein -T$^1$ is linear C$_{1-6}$alkyl;
to form a compound of formula (IV);
  hydrolyzing the compound of formula (IV) to form a compound of formula (V);
coupling the compound of formula (V) with a compound of formula (VII) to form a compound of formula (VI); and
reacting the compound of formula (VI) with a reducing agent to form a compound of formula (II).

18. The method according to claim 17, wherein the compound of formula (III) is reacted with an amine, NHR$^{N1}$R$^{N2}$, and a sulfinating agent to form the compound of formula (IV), where —R$^{N1}$ and —R$^{N2}$ are as defined according to the compounds of formula (IV).

19. The method according to claim 18, wherein the sulfinating agent is, or comprises, sulfur.

20. A method of preparing a compound of formula (I):

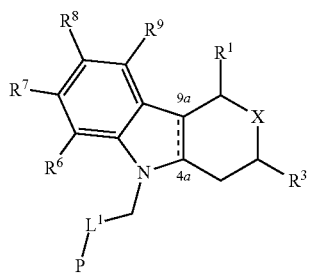

(I)

wherein
—R$^6$, —R$^7$, —R$^8$, and —R$^9$ are each independently —H or —P$^A$;
-L$^1$- is linear C$_{1-6}$alkylene;
—P is independently pyridine or phenyl, optionally substituted with one or more groups —P$^A$;
each —P$^A$ is independently —C$_{1-6}$alkyl
—R$^1$ and —R$^3$ are each independently —H or —C$_{1-6}$alkyl;
and X is independently selected from CH$_2$, CHR$^A$, CR$^A_2$, NH, NR$^A$, O, S, S(O), and S(O)$_2^-$;
said method comprising the method as defined in claim 1 of preparing a compound of formula (II), with the proviso that —R$^{10}$ is —H.

21. The method of claim 20, further comprising the step of reacting the compound of formula (II) with nitrous acid to form a compound of formula (VIII):

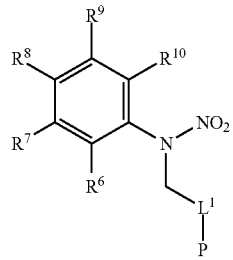

(VIII)

wherein —R$^6$, —R$^7$, —R$^8$, —R$^9$, -L$^1$-, —P and —R$^{10}$ are —H.

22. The method of claim 21 further comprising the step of reacting compound (VIII) with a reducing agent to form a compound of formula (IX):

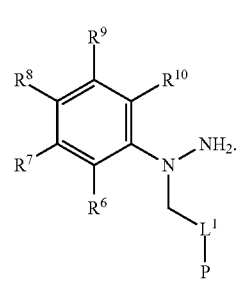

(IX)

23. The method of claim 22, wherein compound (VIII) is reacted with a reducing agent selected from zinc or LiAlH$_4$.

24. The method according to claim 22, further comprising the step of reacting compound (IX) to form compound (I).

25. The method according to claim 24, wherein compound (IX) is reacted with a compound of formula (X):

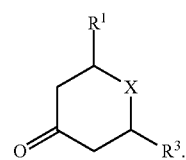

(X)

26. The method according to claim 25, wherein the compound (X) is selected from 1-methyl-piperidin-4-one, tetrahydro-pyran-4-one and tetrahydro-thiopyran-4-one.

27. A compound of formula (I)

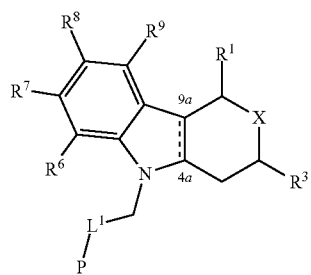

(I)

wherein
- —$R^6$, —$R^7$, —$R^8$, and —$R^9$ are each independently —H or —$P^A$
- -$L^1$- is linear $C_{1-6}$alkylene;
- —P is independently pyridine or phenyl, optionally substituted with one or more groups —$P^A$;
  each —$P^A$ is $C_{1-6}$alkyl;
  and wherein
- —$R^1$ and —$R^3$ are each independently —H or —$C_{1-6}$alkyl;
  X is selected from O, S, S(O) or S(O)$_2$;
and the dashed line indicates that the bond is a single bond or a double bond between the 4a and 9a atoms.

* * * * *